(12) United States Patent
Morris et al.

(10) Patent No.: US 11,747,310 B2
(45) Date of Patent: Sep. 5, 2023

(54) METHODS FOR LIQUID CHROMATOGRAPHY CALIBRATION FOR RAPID LABELED N-GLYCANS

(71) Applicant: WATERS TECHNOLOGIES CORPORATION, Milford, MA (US)

(72) Inventors: Michael F. Morris, Ashland, MA (US); Matthew A. Lauber, North Smithfield, RI (US); Darryl W. Brousmiche, Grafton, MA (US)

(73) Assignee: Waters Technologies Corporation, Milford, MA (US)

( * ) Notice: Subject to any disclaimer, the term of this patent is extended or adjusted under 35 U.S.C. 154(b) by 560 days.

(21) Appl. No.: 16/664,403

(22) Filed: Oct. 25, 2019

(65) Prior Publication Data

US 2020/0124574 A1 Apr. 23, 2020

Related U.S. Application Data

(63) Continuation of application No. 15/526,325, filed as application No. PCT/US2015/060326 on Nov. 12, 2015, now Pat. No. 10,502,720.

(Continued)

(51) Int. Cl.
  *G01N 30/00* (2006.01)
  *G01N 30/02* (2006.01)
  (Continued)

(52) U.S. Cl.
  CPC .......... *G01N 30/02* (2013.01); *B01D 15/305* (2013.01); *C07D 215/48* (2013.01); *C07H 15/26* (2013.01); *G01N 30/04* (2013.01); *G01N 30/88* (2013.01); *G01N 33/6842* (2013.01); *G01N 2030/027* (2013.01); *G01N 2030/047* (2013.01); *G01N 2030/626* (2013.01);
  (Continued)

(58) Field of Classification Search
  CPC ....................................................... G01N 30/02
  USPC ................................................................ 436/14
  See application file for complete search history.

(56) References Cited

U.S. PATENT DOCUMENTS 2,016,962 A 10/1935 Flint et al.
4,068,528 A 1/1978 Gundelfinger
(Continued)

FOREIGN PATENT DOCUMENTS

CN 1211622 A 3/1999
CN 102690833 A 9/2012
(Continued)

OTHER PUBLICATIONS

EP12836127.6 Opposition Communication Jul. 23, 2019. 25 pages.
(Continued)

*Primary Examiner* — Christine T Mui
*Assistant Examiner* — Emily R. Berkeley
(74) *Attorney, Agent, or Firm* — Womble Bond Dickinson (US) LLP; Deborah M. Vernon; Scott R. Breining

(57) ABSTRACT

Methods are provided for making rapid labeled dextran ladders and other calibrants useful in liquid chromatography. The methodologies include a two-step process comprising a reductive amination step of providing a reducing glycan and reacting it with a compound having a primary amine to produce an intermediate compound. The intermediate compound is then rapidly tagged with a rapid tagging reagent to produce the rapid labeled dextran ladder.

1 Claim, 12 Drawing Sheets

Related U.S. Application Data

(60) Provisional application No. 62/079,460, filed on Nov. 13, 2014.

(51) Int. Cl.
  B01D 15/30 (2006.01)
  C07D 215/48 (2006.01)
  G01N 30/04 (2006.01)
  C07H 15/26 (2006.01)
  G01N 30/88 (2006.01)
  G01N 33/68 (2006.01)
  G01N 30/62 (2006.01)

(52) U.S. Cl.
  CPC . G01N 2030/8836 (2013.01); G01N 2400/00 (2013.01); G01N 2440/38 (2013.01)

(56) References Cited

U.S. PATENT DOCUMENTS

| | | | |
|---|---|---|---|
| 5,531,959 | A | 7/1996 | Johnson et al. |
| 6,379,971 | B1 | 4/2002 | Schneider et al. |
| 6,716,634 | B1 | 4/2004 | Myerson |
| 7,074,570 | B2 | 7/2006 | Palmgren et al. |
| 7,186,739 | B2 | 3/2007 | Guichard et al. |
| 7,732,378 | B2 | 6/2010 | Thompson et al. |
| 8,198,063 | B1 | 6/2012 | Baginski et al. |
| 10,416,166 | B2 | 9/2019 | Brousmiche et al. |
| 2004/0259262 | A1 | 12/2004 | Ishii |
| 2005/0221337 | A1 | 10/2005 | Seeberger et al. |
| 2006/0127950 | A1 | 6/2006 | Bosques et al. |
| 2006/0270048 | A1* | 11/2006 | Dwek ............... G01N 33/582 436/67 |
| 2007/0141723 | A1 | 6/2007 | Sompuram et al. |
| 2007/0269895 | A1 | 11/2007 | Aebersold et al. |
| 2008/0201095 | A1 | 8/2008 | Yip et al. |
| 2009/0050212 | A1 | 2/2009 | Dourdeville et al. |
| 2009/0065687 | A1 | 3/2009 | Gross et al. |
| 2010/0151499 | A1 | 6/2010 | Collins et al. |
| 2010/0171055 | A1 | 7/2010 | Dourdeville |
| 2011/0006237 | A1 | 1/2011 | Tower |
| 2013/0112604 | A1 | 5/2013 | Keene et al. |
| 2013/0171658 | A1 | 7/2013 | Fulton et al. |
| 2014/0030732 | A1 | 1/2014 | Staples |
| 2014/0038215 | A1 | 2/2014 | Smart et al. |
| 2014/0178912 | A1 | 6/2014 | Liu et al. |
| 2014/0200148 | A1 | 7/2014 | Slade |
| 2014/0227793 | A1 | 8/2014 | Gao et al. |
| 2014/0242709 | A1 | 8/2014 | Brousmiche et al. |
| 2014/0274768 | A1 | 9/2014 | Haab |
| 2014/0350263 | A1 | 11/2014 | Brousmiche et al. |
| 2014/0370614 | A1 | 12/2014 | Liu et al. |
| 2015/0057243 | A1 | 2/2015 | Zhou et al. |
| 2015/0204824 | A1 | 7/2015 | Lauber et al. |
| 2016/0018409 | A1 | 1/2016 | Higel |
| 2016/0054274 | A1 | 2/2016 | Cormier et al. |
| 2016/0069844 | A1 | 3/2016 | Jackson et al. |
| 2016/0139136 | A1 | 5/2016 | Brousmiche et al. |
| 2017/0370813 | A1 | 12/2017 | Steen et al. |

FOREIGN PATENT DOCUMENTS

| | | | |
|---|---|---|---|
| CN | 103918055 | A | 7/2014 |
| EP | 2305692 | A1 | 4/2011 |
| EP | 2990401 | A1 | 3/2016 |
| JP | S59161355 | A | 9/1984 |
| JP | S62195361 | A | 8/1987 |
| JP | H09101310 | A | 4/1997 |
| JP | 2000329744 | A | 11/2000 |
| JP | 2001526048 | A | 12/2001 |
| JP | 2006038674 | A | 2/2006 |
| JP | 2012512234 | A | 5/2012 |
| WO | 9921580 | A1 | 5/1999 |
| WO | 02074245 | A2 | 9/2002 |
| WO | 2004086050 | A2 | 10/2004 |
| WO | 2013081581 | A1 | 6/2013 |
| WO | 2013151975 | A1 | 10/2013 |
| WO | 2013192530 | A2 | 12/2013 |
| WO | 2014085938 | A1 | 6/2014 |
| WO | 2014194320 | A1 | 12/2014 |
| WO | 2016009077 | A1 | 1/2016 |
| WO | 2016089515 | A1 | 6/2016 |

OTHER PUBLICATIONS

Expert Declaration by Prof. Ulf Diederichsen dated Jul. 23, 2019, 7 pp.
Kuster, B., et al: "Structural Determination of N-linked carbohyrdrates by matrix-assisted laser desorption/ionization-mass spectrometry following enzymatic release within sodium dodecyl sulphate-polyacrylamide electrophoresis gels: application to species-specific glycosylation of a1-acid glycoprotein", Electrophoresis 19:1950-1959 (1998).
Yodoshi, M., et al.: "Optimized conditions for high-performance liquid chromatography analysis of oligosaccharides using 7-amino-4-methylcoumarin as a reductive amination reagent", Journal of Chromatography A 1203(2):137-145 (2008).
Extended European Search Report and Written Opinion for EP Application No. 15855907.0 dated Mar. 19, 2018, 10 pages.
Communication pursuant to Article 94(3) EPC, dated Apr. 17, 2019, for Application No. EP15855907.0, 4 pages.
Bereman et al., "Increasing the hydrophobicity and electrospray response of glycans through derivatization with novel cationic hydrazides", Chem Commun (Camb) 46(2): 237-9 (2010).
Ciucanu et al., "A Simple and Rapid Method for the Permethylation of Carbohyrates", Carbohydr. Res. 131, 209-217 (1984).
Cook, et al., "Development and Qualification of an Antibody Rapid Deglycosylation Method", Biologicals 40(2):109-17 (2012).
Gong et al., "N-Glycosylamine-Mediated Isotope Labeling for Mass Spectrometry-Based Quantitative Analysis of N-linked Glycans", Anal Bioanal Chem 405: 5825-31 (2013).
Harvey, D.J., "Electrospray Mass Spectrometry and Fragmentation of N-Linked Carbohydrates Derivatized at the Reducing Terminus", J Am Soc Mass Spectrom 11(10):900-15 (2000).
Harvey, et al., "Proposal for a standard system for drawing structural diagrams of N- and O-linked carbohydrates and related compounds", Proteomics 9(15): 3796-801 (2009).
International Search Report and Written Opinion for International App. No. PCT/US15/57848, dated Feb. 5, 2016, 5 pages.
Lauber et al., "Optimization of GlycoWorks HILIC SPE for the Quantitative and Robust Recovery of N-Linked Glycans from mAb-Type Samples", Waters Application Note (2013) 9 pages.
Liu et al., "Investigation of Sample Preparation Artifacts Formed during the Enzymatic Release of N-Linked Glycans prior to Analysis by Capillary Electrophoresis", Anal. Chem. 81: 6823-6829 (2009).
Mechref et al., "Quantitative Glycomics Strategies", Mol Cell Proteomics 12 (4) 874-84 (2013).
Pettersson et al., "Chemical Stability of Reversed Phase High Performance Liquid Chromatography Silica under Sodium Hydroxide Regeneration Conditions", J Chromatogr A 1142 (1 ): 93-97 (2007).
Ruhaak et al., "Glycan labeling strategies and their use in identification and quantification", Anal Bioanal Chem 397(8), 3457-3481 (2010).
Walker et al., "Hydrophobic Derivatization of N-linked Glycans for Increased Ion Abundance in Electrospray onization Mass Spectrometry", J Am Soc Mass Spectrom 22(8):1309-17 (2011).
GlykoPrep™ Instant AB now fully commercialised [online] [retrieved on Sep. 8, 2014]. Retrieved from Internet URL: http://www.eropa-bioproducts.com/latest.aspx?id=14.
Extended European Search Report for Application No. 17767589.9, dated Jan. 30, 2020, 11 pages.
International Search Report and Written Opinion for International Application No. PCT/US17/38073, dated Sep. 12, 2017, 10 pages.
Song, X., et al., "Glycan microarrays off fluorescently-tagged natural glycans", Glycoconjugate Journal, 32:465-473 (2015).

(56) References Cited

OTHER PUBLICATIONS

Schwartz, B., et al., "A Kinetic Characterization of the Glycosyltransferase Activity of *Eschericia coli* PBP1b and Development of a Continuous Fluorescence Assay", Biochemistry, 41:12552-12561 (2002).
Bunz, S-C., et al., "Analysis of native and APTS-labeled N-glycans by capillary electrophoresis/time-0f-flight mass spectrometry", Analytical and Bioanalytical Chemistry 405:8277-8284 (2013).
Knezevic, A., et al., "High throughput plasma N-glycome profiling using multiplexed labelling and UPLC with fluorescence detection", Analyst, 136:4670 (2011 ).
Lauber, M.A. et al., "Rapid Preparation of Released N-Glycans for HILIC Analysis Using a Labeling Reagent that Facilitiates Sensitive Fluorescence and ESI-MS Detection", Analytical Chemistry 87:5401-5409 (2015).
Extended European Search Report for EP Application No. 17815987.7, dated Dec. 16, 2019, 8 pages.
Extended European Search Report for Application No. EP17820918.5, dated Jan. 28, 2020, 7 pages.
Paschinger, K., et al., "Analysis of zwitterionic and anionic N-linked glycans from invertebrates and protists by mass spectrometry", Glycoconjugate Journal, 33(3):273-283 (2016).
Qu, Y., et al., "Structural analysis of N- and O-glycans using ZIC-HILIC/dialysis coupled to NMR detection", Fungal Genetics and Biology, 72:207-215 (2014).
Author unknown, Best Practices in the Analysis of Rapifluor-MS Labeled Glycans Using the Acquity QDa Detector 5 Performance Model, Waters [online] Mar. 2016 While Paper [retrieved on Apr. 1, 2020]. Retrieved from the internet URL: https://www.gimitec.com//file/720005655en.pdf, 19 pages.
Extended European Search Report for EP 20188814.6 , dated Oct. 2, 2020, 7 pages.
Johannesen et al. "Glycan analysis via derivatization with a fluorogenic pyrylium dye", Carbohydrate Research, 352: 94-100 (2012). Abstract.
International Search Report and Written Opinion for International Application No. PCT/US2017/038070, dated Sep. 29, 2017, 10 pages.
PubChem CID: 43450869 Create Date: Jul. 21, 2009.
Struwe et al. 'Aminoquinolines as fluorescent labels for hydrophilic interaction liquid chromatography of oligosaccharides'. Biological Chemistry, 2012, vol. 393, pp. 757-765.
International Search Report and Written Opinion for International Application No. PCT/US2017/038072, dated Oct. 3, 2017, 9 pages.
Tousi, "The Pursuit of Cancer Biomarkers: Liquid Chromatography and Mass Spectrometry 1-13 Platforms for Glycomic Characterization of Biospecimens" Northeastern University, Jul. 16, 2013.
Yang et al., "Solid-phase glycan isolation for glycomics analysis", Proteomics Clin Appl. 6(0): 596-608. (2012).
Pall Life Sciences "AcroPrep Advance Filter Plates" Pall Corporation (Mar. 2013) p. 7, col. 2, 10 Table AcroPrep Advance 96-Well Filter Plates for Ultrafiltration.
Roth, "Charge Derivatization of Peptides for Analysis by Mass Spectrometry," Mass Spectrometry Reviews 1998, 17(4):255-274. Abstract.
Schwartz, "Systematic Delineation of Scan Modes in Multidimensional Mass Spectrometry," Anal. Chem. 1990, 62(17):1809-1818. Abstract.
Cohen, "Clearing the Hurdle of High Sensitivity in Biopharmaceutical Research," LC GC North America 1999, 17(4S): S9-S16.
Vollhardt, "Organic Chemistry Structure and Function," Third Edition, W. H. Freeman and Company, 1999, Chapters 14,20, 21, 26. Abstract.
Voet, "Biochemistry" Second Edition, John Wiley & Sons, Inc. 1995, Chapters 4, 5. Abstract.
Snyder, "Introduction to Modern Liquid Chromatography," Second Edition, John Wiley & Sons, Inc. 1979, Introduction, Chapters 2, 4, 13, 14, 17. Abstract.
Synder, "Practical HPLC Method Development," Second Edition, John Wiley & Sons, Inc. 1997, Chapters 3, 4. Abstract.
Lawrence, "Derivatization in Chromatography Introduction, Practical Aspects of Chemical Derivatization in Chromatography," Journal of Chromatographic Science 1979, 17:113-114. Abstract.
Jupille, "UV-Visible Absorption Derivatization in Liquid Chromatography," Journal of Chromatographic Science 1979, 17:160-167. Abstract.
Amendment and Response in response to Office Action dated Jun. 30, 2011, in U.S. Appl. No. 12/365,880, filed Feb. 4, 2009.
Chapter 2—Norepinephrine cited during EP3472132 examination procedure dated Jul. 16, 2020.
Chinese Office Action for Patent Application No. 201810988090.8 dated Mar. 23, 2021, original and translated documents, 25 pages.
CNOA for application 201580071764.2 dated Feb. 28, 2020 original and translated document, 18 pages.
CNOA for Patent Application No. 201780053453.2 dated Feb. 4, 2021, original and translated document 24 pages.
Communication pursuant to Article 94(3) EPC for EP Application No. 17820918.5, dated May 25, 2021, 5 pages.
Communication pursuant to Article 94(3) EPC in European Patent Application No. 17815987. 7, dated Dec. 4, 2020, 5 pages.
Communication pursuant to Article 94(3) EPC, for Application No. EP17820918.5, dated Nov. 26, 2020, 5 pages.
EP Communication with extended search report, EP Application No. 15180680.9, dated Feb. 2, 2016.
Huang, R., ed., Analytical Chemistry, National Defense Science and Technology University Press pp. 146-150 (Mar. 2014).
Li De et al.,"Techniques of Biomolecule Scientific Experiments", Hunan Science and Technology Press, Nov. 2001, the 1st edition, p. 32-33.
Neville, D.C.A., et al., "Development of a Single Column Method for the Separation of Lipid- and Protein-Derived Oligosaccharides", Journal of Proteome Research, 8(2):681-687 (2009).
Nimura, "Detection reagents used for high performance liquid chromatography," Pharmacia (1981) 17(8):707-709.
Non-Final Office Action, U.S. Appl. No. 14/193,418, dated Nov. 15, 2016.
Non-Final Office Action, U.S. Appl. No. 14/342,131, dated Nov. 4, 2016.
Notice of Rejection, JP Application No. 2014-533416, dated Jan. 10, 2017. Original and Translated.
Office Action, U.S. Appl. No. 14/458,760, dated Apr. 12, 2017.
Notice for Reasons for Rejection, dated Jul. 23, 2012, in Japanese Application No. 2009-269796 OD and Trans.
Response to EP Communication with extended search report, EP Application No. 15180680.9, dated Sep. 2, 2016.
Response to Non-Final Office Action, U.S. Appl. No. 14/342,131 dated Feb. 6, 2017.
Response to Non-Final Office Action, U.S. Appl. No. 14/193,418, dated Feb. 15, 2017.
Response to Office Action, U.S. Appl. No. 14/458,760, dated Jun. 12, 2017.
Response to Restriction Requirement, U.S. Appl. No. 14/342,131 dated Sep. 28, 2016.
Restriction Requirement, U.S. Appl. No. 14/342,131, dated Aug. 17, 2016.
Waters Corporation "GlycoWorks High-Throughput Sample Preparation Kit" (Sep. 2013).
West, C., et al., "Porous Graphitic Carbon: a Versatile Stationary Phase for Liquid Chromatography", J Chromatogr A 1217(19):3201-16 (2010).
Zhang Li et al., "Practical Guidance of Detection by Separation", Press of University of Science and Technology of China, Jan. 2013, p. 55.
Zhang, Y., ed., Biological Sample Library Establishment and Practice, p. 102 Sun Yat-Sen University Press (Oct. 2013).
Kim, J.Y., et al., "Development of an Online Microbore Hollow Fiber Enzyme Reactor Coupled with Nanoflow Liquid Chromatography—Tandem Mass Spectrometry for Global Proteomics", Analytical Chemistry 85:5506-5513 (2013).
Rahman, S.A. et al., "Filter-Aided N-Glycan Separation (FANGS): A Convenient Sample Preparation for Mass Spectrometric N-Glycan Profiling" J. Proteome Res 13:1167-1176 (2014).

(56) References Cited

OTHER PUBLICATIONS

Yang, et al., "Glycan Analysis by Isobaric Aldehyde Reactive Tags and Mass Spectrometry", Anal Chem 85(17):8188-8195 (2013).
Fekkes, Durk, "State-of-the-Art of High-Performance Liquid Chromatographic Analysis of Amino Acids in Physiological Samples," Journal of Chromatography B. 1996, 682(1):3-22.
De Hoffmann, "Mass Spectrometry, Principles and Applications," Second Edition, John Wiley & Sons Ltd. 2001, Introduction, Chapters 1, 3, and 7. Abstract.
Watson, "Introduction to Mass Spectrometry" Raven Press, New York 1985, Chapters 1 and 4. Abstract.
McLafferty, "Interpretation of Mass Spectra," Fourth Edition, University Science Books, Sausalito, CA 1993, Chapter 1. Abstract.
Covey, "Liquid Chromatography/Mass Spectrometry," Analytical Chemistry 1986, 58(14): 1451A-1461A. Abstract.
Chalmers, "Advances in Mass Spectrometry for Proteome Analysis," Current Opinion in Biotechnology 2000, 11: 384-390. Abstract.
Keough, "Atmospheric Pressure Matrix-Assisted Laser Desorption/Ionization Ion Trap Mass Spectrometry of Sulfonic Acid Derivatized Tryptic Peptides," Rapid Communications in Mass Spectrometry 2001, 15(23): 2227-2239. Abstract.
Yost, "Triple Quadrupole Mass Spectrometry for Direct Mixture Analysis and Structure Elucidation," Analytical Chemistry 1979, 51(12):1251A-1264A. Abstract.
Ma, "Determination of Midazolam and its Metabolites in Microsamples by High-Performance Liquid Chromatography and its Application to Pharmacokinetics in Rats," J Chromatography B Biomed Appl. 1996, 682(1):109-113. Abstract.
Buku, A., et al., "2,3-trans-3,4-trans-3,4-Dihydroxy-L-proline: An Amino Acid in Toxic Peptides of *Amanita virosa* Mushrooms,"Proc. Natl. Acad. Sci. USA, 1980, 77(5): 2370-2371.
Yates, J.R., et al., "Peptide Mass Maps: A Highly Informative Approach to Protein Identification," Analytical Biochemistry 1993, 214: 397-408.
Cech and Enke, "Relating Electrospray Ionization Response to Nonpolar Character of Small Peptides," Anal. Chem. 2000, 72:2717-2723. Abstract.
HP Primer Hewlett Packard, Basics of LC/MS: A Primer. 1998.
De Hoffmann, "Tandem Mass Spectrometry: a Primer," J. Mass Spec. 1996, 31, 129-137. Abstract.
Louris, "New Scan Modes Accessed with a Hybrid Mass Spectrometer," Anal. Chem. 57(14):2916-2924 (1985).
Brancia, F.L., et al., "Improved matrix-assisted laser desorption/ionization mass spectrometric analysis of tryptic hydrosylates of proteins following guanidation of lysine-containing peptides," Rapid Commun. Mass Spectrom. 14:2070-2073 (2000) Abstract.
Quirke, J.M., et al., Chemical Derivatization for Electrospray Ionization Mass Spectrometry. 1. Alkyl Halides, Alcohols, Phenols, Thiols, and Amines,II Anal Chem. 1994, 66, 1302-1315. Abstract.
Morpugo, "N-hydroxysuccinimide carbonates and carbamates are useful reactive reagents for coupling ligands to lysines on proteins," J. Biochem. Biophys. Methods 38 (1999), 17-28.
Shimbo, K., et al., "Multifunctional and Highly Sensitive Precolumn Reagents for Amino Acids in Liquid Chromatography/Tandem Mass Spectrometry," Anal. Chem. 2009, 81, 5172-5179. Abstract.
Brophy, "Electron Impact and chemical ionization mass spectra of aryl ureas," Organic Mass Spectrometry, vol. 14, No. 7, 1979, 379-386. Abstract.
Rudd, P., et al., "Rapid, sensitive sequencing of oligosaccharides from glycoproteins," Current Opinion in Biotechnology 1997, 8:488-497.
Iwaki, K., et al., "Activated carbamate reagent as chiral derivatizing agent for liquid chromatographic optical resolution of enantiomeric amino compounds," Chromatographia 1987, 23(12), 899-902. Abstract.
Iwaki, K., et al., "Amino acid analysis by reversed-phase high performance liquid chromatography automatic pre-column derivatization with activated carbamate reagent", Journal of Chromatography, 407 (1987) 273-279. Abstract.
Byrnes, "6-Aminoquinoline as a Fluorogenic Leaving Group in Peptide Reactions: A New Fluorogenic Substrate for Chymotrypsin," Anal. Biochem. 116, 408-413 (1981). Abstract.
Busto, "Solid phase extraction of biogenic amines from wine before chromatographic analysis of their AQC derivatives," J. Liq. Chrom. & Rel. Technol. 1997, 20(5), 743-755. Abstract.
Hirai, "Development of a new fluorescence labeling reagent succinimido-2-fluorenylcarbamate for highly sensitive detection of Nsolanesyl-N,N-bis(3,4-dimethoxybenzyl)ethanediamine by HPLC," Anal. Chem. 1991, 40(5), 233-238. Abstract.
EP Communication under Rule 71(3) EPC, EP Application No. 12836127.6, dated Mar. 15, 2017.
Bartlet-Jones, "Peptide ladder sequencing by mass spectrometry using a reagent," Rapid Commun. Mass Spectrom. 1994, 8, 737-742. Abstract.
Spengler, "Peptide sequencing of charged derivatives by postsource decay MALDI mass spectrometry," Int. J. Mass Spectrom. Ion Processes 1997, 169/170, 127-140. Abstract.
Hermanson, G.T., et al., "Bioconjugate Techniques," 1996, Chapter 8. Abstract.
Dell, A., et al., "Fast Atom Bombardment Mass Spectrometric Strategies for Characterizing Carbohydratecontaining Biopolymers," Biomedical and Environmental Mass Spectrometry, 1998, 16, 19-24. Abstract.
Nakashima, K., et al., "Study on π-π Interaction in High Performance Liquid Chromatography," J. Liq. Chrom. & Rel. Technol. 2000, 23(16), 2533-2540. Abstract.
Okamoto, M., et al., "Sensitive Detection and Structural Characterization of Trimethyl(p-aminophenyl)-ammonium-derivatized Oligosaccharides by Electrospray Ionization-Mass Spectrometry and Tandem Mass Spectrometry", Rapid Communications in Mass Spectrometry, 1995, 9, 641-643. Abstract.
Rasmussen, "The nomenclature of fused-ring arenes and heterocycles: a guide to an increasingly important dialect of organic chemistry," ChemTexts, 2016, 2(16), 1-13.
Reubsaet, J.L., et al., "Characterisation of p-p interactions which determine retention of aromatic compounds in reversed-phase liquid chromatography," Journal of Chromatography A, 1999, 841, 147-154.
Schwartz, J.C., "Multistage mass spectrometry: Scan modes and new instrumentation" Dissertation 1989.
Stoeckmann, "Ultrahigh Throughput, Ultrafiltration-Based N-Glycomics Platform for Ultraperformance Liquid Chromatography (ULTRA3)," Anal. Chem. 2015, 87, 8316-8322. Abstract.
Block, E.H., "The Use of 6-Aminoquinolyl-N-Hydroxy Succinimidyl Carbamate Derivatives for HPLC/MS Analysis of Amino Acids", AMD35 Waters Alliance LC/MS System 2000.
Cline, G.W., and Hanna, S.B., "The Aminolysis of N-Hydroxysuccinimide Esters. A Structure-Reactivity Study", J Am Chem Soc 109(10):3087-3091 (1987).
Communication pursuant to Article 94(3) EPC for Application No. EP17188121.2, dated Sep. 14, 2020, 3 pages.
EP Communication pursuant to Article 94(3) EPC, EP Application No. 12836127.6, dated Sep. 26, 2016.
H. R. Liang, et al., "Quantitative determination of endogenous sorbitol and fructose in human nerve tissues by atmospheric-pressure chemical ionization liquid chromatography tandem mass spectrometry", Rappid Communications in Mass Spectrometry, 19(16):2284-2294, Aug. 30, 2005. Abstract.
Heindel, N.D., et al., "Diaminoquinoline antimalarials", J. Med. Chem. 12(5):797-801 (1969).
Higuchi, K., et al., "Chemistry of Succinimido Esters. IV*1. A Facile Preparation of N-Succinimidyl Carboxylates Using N, N'-Disuccinimidyl Carbonate", Oil Chemistry, 36(1):16-20 (1987).
International Search Report and Written Opinion for International application No. PCT/GB2016/051605 dated Sep. 15, 2016.
Search Report for GB1509402.2 dated Mar. 1, 2016.
Eoin FJ Cosgrave and Sean M McCarthy, Investigation of the Factors that Contribute to Glycan Separation in HI LIC, Business Operations, Pharmaceutical Life Sciences, Waters Corporation (Year: 2014) 4 pages.
Statement of grounds appeal for European patent application No. 15180680.9, dated May 20, 2020, 4 pages.

(56) References Cited

OTHER PUBLICATIONS

Summons to attend oral proceedings pursuant to Rule 115(1) EPC for Application No. EP15180680.9, dated Jul. 18, 2019, 4 pages.
Summons to attend oral proceedings pursuant to Rule 115(1) EPC for Application No. EP15180680.9, dated Jun. 17, 2019, 9 pages.
Registry File from STN for compound RN 1975675-34-3, entered on STN Aug. 19, 2016, downloaded Sep. 8, 2020 (Year: 2016).
Bioengineering Analysis and Inspection, Wang Furong China Light Industry Press pub. Jun. 30, 2005.
Fu-Chuan, Li, et al., "Studies on Fluorescent Labeling of Marine Sulfated Polysaccharide 911", Chemical Journal of Chinese Universities, 23(9):1704-1708 (2002).
Zailin, W., "Studies on Fluorescent Labeling of Several Fungal Polysaccharides", Chinese Master's Thesis, Agriculture Science and Technology, No. 5 (2013).
Registry File from STN for compound RN 1915940-97-4, entered on STN May 23, 2016, downloaded Sep. 8, 2020 (Year: 2016).
European Search Report for Application No. 15855907.0, dated Jul. 6, 2018, 12 pages.
Harvey, D.J., "Derivatization of carbohydrates for analysis by chromatography: electrophoresis and mass spectrometry", Journal of Chromatography B 879(17-18):1196-1225 (2010). Abstract.
Registry File from STN for compound RN 1977407-60-5, entered on STN Aug. 22, 2016, downloaded Sep. 8, 2020 (Year: 2016).
Registry File from STN for compound RN 1919202-16-6, entered on STN May 27, 2016, downloaded Sep. 8, 2020 (Year 2016).
Registry File from STN for compound RN 1970079-84-5, entered on STN Aug. 9, 2016, downloaded Sep. 8, 2020 (Year: 2016).
Extended European Search Report for EP application No. 20188814.6, dated Oct. 2, 2020, 7 pages.

* cited by examiner

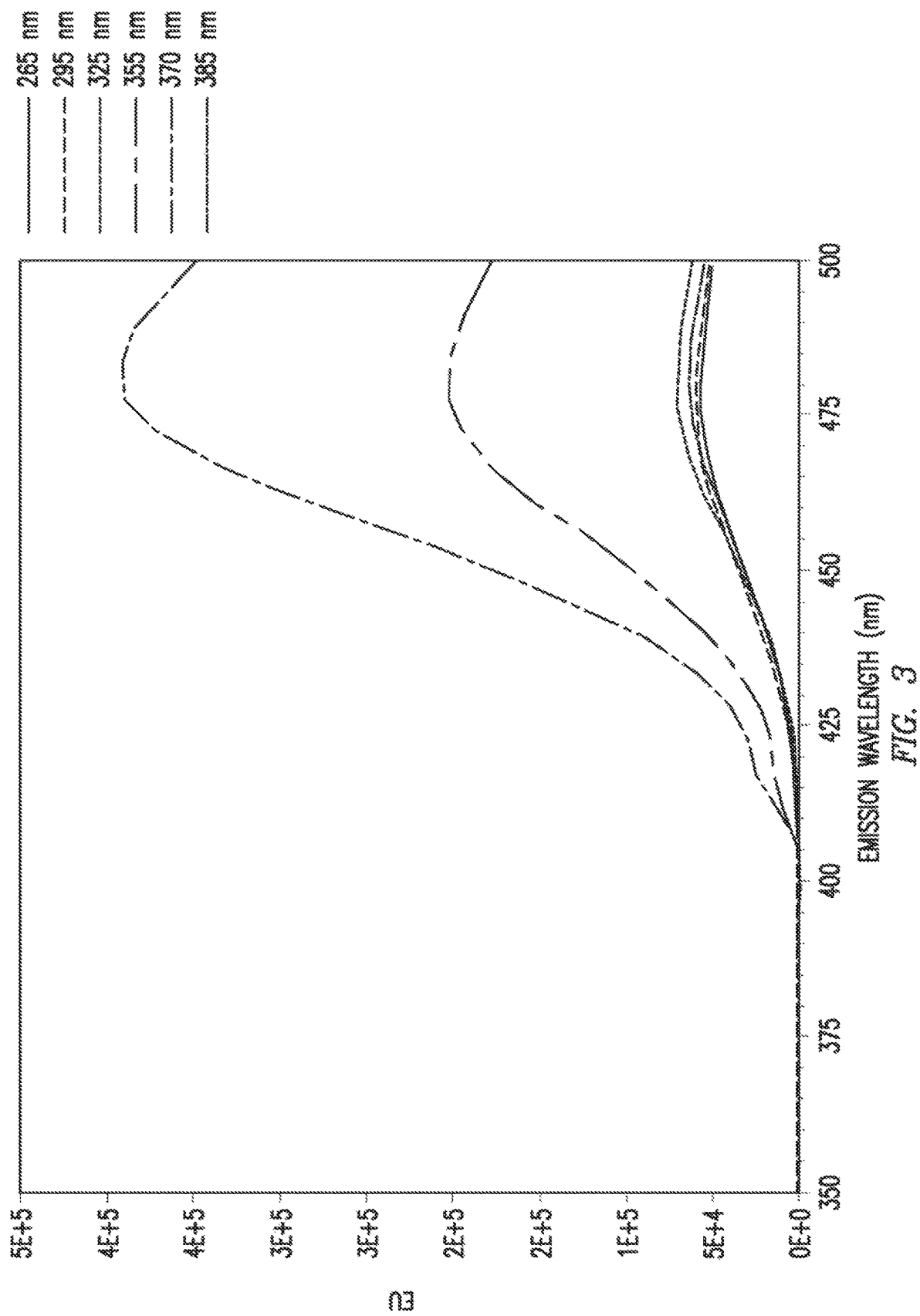

METHODS FOR LIQUID CHROMATOGRAPHY CALIBRATION FOR RAPID LABELED N-GLYCANS

CROSS REFERENCE TO RELATED APPLICATIONS

This application is a divisional application of U.S. patent application Ser. No. 15/526,325, filed May 11, 2017, which is the National Stage of International Patent Application No. PCT/US15/60326, filed Nov. 12, 2015, which claims priority from and the benefit of U.S. Provisional Patent Application No. 62/079,460, filed on Nov. 13, 2014. The disclosure of each of the preceding applications is hereby incorporated by reference in its entirety.

BACKGROUND OF THE INVENTION

Hydrophilic interaction chromatography ("HILIC") separation coupled with fluorescence detection in UPLC platforms can be used to resolve complex N-linked glycan populations due to the ability to separate both neutral and charged glycans in a single chromatographic run. Because of the heterogeneity, isomerization and anomericity of glycans, elucidating the structure of complex N-linked glycans can be a significant analytical challenge. A dextran ladder can be used to calibrate hydrophilic interaction chromatography ("HILIC") separations of glycans and convert peak retention times into glucose unit ("GU") values. Each individual glycan structure has a GU value which is directly related to its linkages and its constituent monosaccharides. The GU value can be used to predict structures because each glycan structural component contributes in a specific way to the GU value of a given glycan.

As such, the elution times of glycans can be expressed in glucose units by reference to a separation calibrant, such as one based on a dextran ladder. A dextran ladder can be used to calibrate the liquid chromatography ("LC") runs against day-to-day or system-to-system changes. A GU value can be calculated by fitting a fifth order polynomial distribution curve or a cubic spline fit to the retention times of the dextran ladder. Then, using this curve, GU values can be assigned from the retention times observed in a test sample. The GU values for N-glycans can be reproducible, with inter-column standard deviations less than 0.3. This allows direct comparison with database values collected from a range of instruments over a period of time. Having GU values, databases of glycans stored in values of GU can be interrogated to aid in elucidating the potential glycan structures existing with a glycan population.

Furthermore, even when comparing different approaches for tagging, it can be seen that the labeled N-glycans are resolved by the HILIC separation into very similar profiles. It is not a trivial task to produce a dextran ladder that is appropriate for use with glycans that are rapidly labeled with a rapid tagging reagent. Dextran is a saccharide comprised of a reducing, aldehyde terminus, different than N-glycosylamines which are released via enzymatic deglycosylation of N-glycosylated proteins. Unlike the latter, dextran cannot therefore be modified with a rapid tagging reagent that targets amine nucleophiles. The dextran cannot be rapidly labeled because the saccharide does not contain an appropriate nucleophile. A need exists, as a result, for methods of calibrating the liquid chromatography processes with a standard that has the same optical and/or other physiochemical properties as the rapid labeled N-glycan.

SUMMARY OF THE INVENTION

Methods of making a rapid labeled dextran ladder and other calibrants useful in liquid chromatography are provided herein. The methods comprise the steps of providing a reducing glycan having an aldehyde group and reacting the reducing glycan with a compound having a primary amine to produce an intermediary compound. The intermediary compound is rapidly labeled with the rapid tagging reagent to produce a rapid labeled dextran ladder having substantially identical optical properties as a rapid labeled N-glycan produced by rapid tagging of the N-glycan with the rapid tagging reagent. Calibrants are also provided herein of the structural formula:

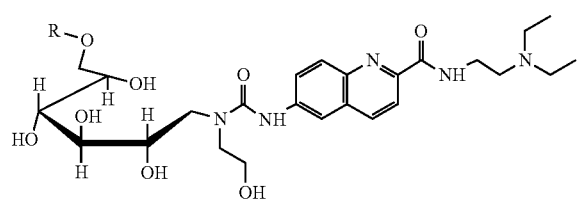

wherein R is a glucose unit or a monosaccharide unit. The methods provided herein are useful for rapid tagging or dual tagging compounds containing an aldehyde group.

BRIEF DESCRIPTION OF THE DRAWINGS

FIG. 3 shows fluorescence emission spectra for a dextran ladder labeled with analog of a rapid tagging reagent by reductive amination only having shifted fluorescence properties of optimized wavelengths of 370 nm for excitation and 480 nm for emission.

DETAILED DESCRIPTION

Figure 1:
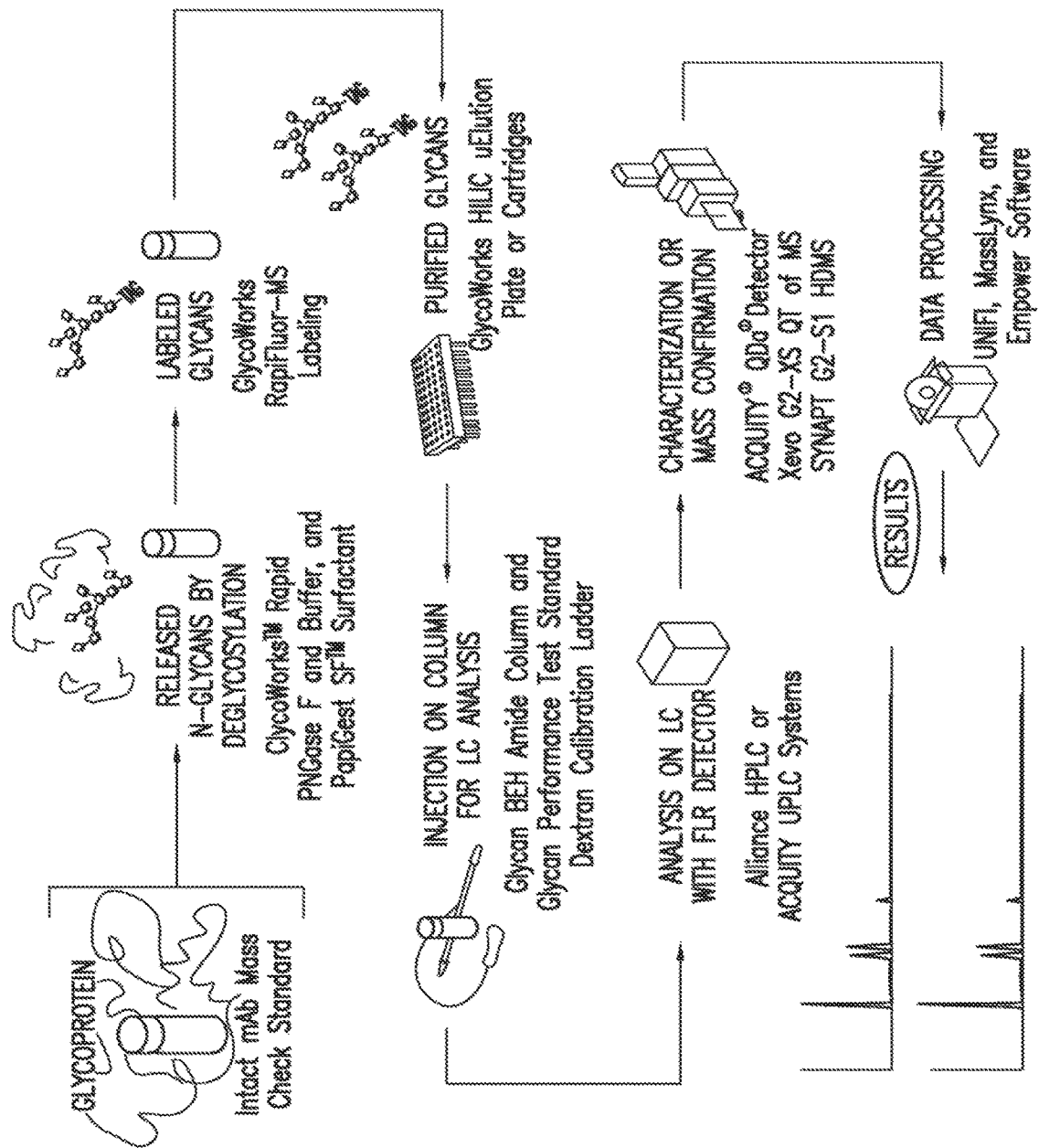
FIG. 1 shows an embodiment of workflow for preparing a rapid labeled N-glycan.

In the manufacturing of biopharmaceuticals, glycosylation profiles of biological samples are often assessed through an analysis of released glycans. These samples, however, are often prepared with techniques that are time-consuming or ones that can lead to a compromise in mass spectrometry ("MS") sensitivity. Enzymatic release and rapid labeling of N-glycans can address many shortcomings and provide higher throughput of N-glycan sample preparation and enable improved sensitivity for glycan detection. For example, as described herein, with an enzymatic release and rapid labeling of N-glycans, glycoproteins can now be deglycosylated in as low as 10 minutes to produce N-glycans which are then rapidly reacted with rapid tagging reagents. The resulting labeled glycans are then extracted from the labeling reaction byproducts by an SPE method to facilitate analysis of samples.

The N-glycan profile of a biopharmaceutical is a critical quality attribute because it can be a measure of efficacy, safety, and manufacturing conditions. Therefore, approaches for glycan analysis of clinical and commercial bio-therapeutic formulations require high sensitivity. Additionally, when the analysis is performed, rapid turnaround times and high throughput capacity can expedite product development.

Most analytical strategies for evaluating N-glycans from glycoproteins involve deglycosylation via PNGase F and the labeling of the resulting N-glycans with a chemical moiety that imparts a detectable attribute. In one approach described herein, labeled glycans are separated by hydrophilic interaction chromatography ("HILIC") and detected by fluorescence ("FLR") and mass spectrometry ("MS").

Furthermore, we previously developed a sample preparation solution that enables FLR and MS sensitivity for glycan detection while improving throughput of N-glycan sample preparation. We have developed rapid tagging reagents which can be synthesized to rapidly react with N-glycans upon their release from glycoproteins. (Brousmiche, et al., U.S. Published Patent Application No. 2014/0350263, filed Aug. 13, 2014, ¶¶[0008]-[0022], [0047]-[0050], [0053]-[0182], [0191], [0228] and [0230]-[0316], incorporated herein by reference). By utilizing the rapid tagging reagent, within a 5 minute reaction, N-glycans can be labeled. The rapid tagging reagents utilized herein comprise an N-hydroxysuccinimide (NHS) carbamate rapid tagging group, an efficient quinoline fluorophore, and a highly basic tertiary amine for enhancing ionization and are exemplified in Table 1 below.

TABLE 1

Exemplary Rapid Tagging Reagents

| Rapid Tagging Reagent No. | Labeling Reagent Structure | Chemical Name | Other Reagent Reference Names |
|---|---|---|---|
| 1 | | 2,5-dioxopyrrolidin-1-yl (2-((2-(diethylamino)ethyl)carbamoyl)quinolin-6-yl)carbamate | RapiFluor-MS or RFMS |
| 2 | | 2,5-dioxopyrrolidin-1-yl (4-((2-(diethylamino)ethyl)carbamoyl)phenyl)carbamate | |
| 3 | | 2,5-dioxopyrrolidin-1-yl quinolin-6-ylcarbamate | |
| 4 | | 2,5-dioxopyrrolidin-1-yl methylcarbamate | |

TABLE 1-continued

Exemplary Rapid Tagging Reagents

| Rapid Tagging Reagent No. | Labeling Reagent Structure | Chemical Name | Other Reagent Reference Names |
|---|---|---|---|
| 5 |  | 2,5-dioxopyrrolidin-1-yl (4-carbamoylphenyl)carbamate | IAB, or Instant AB |

In the present methods, a reducing saccharide is labeled (tagged) via reductive amination and the resulting secondary amine containing saccharide is rapidly tagged with a rapid tagging reagent. The methodologies presented herein can be used in tagging or dual tagging any compounds containing an aldehyde.

To further accelerate the preparation of N-glycans, use of the rapid tagging reagent can be directly integrated with the PNGase F deglycosylation procedure which further involves a surfactant and a HILIC μElution solid phase extraction ("SPE") clean-up procedure to provide a quantitative recovery of the released and labeled glycans having the added benefit of no solvent dry-down step prior to the liquid chromatography ("LC") analysis of samples.

Example 1

Rapid Preparation of Released N-Glycans HILIC Analysis Using Rapid Tagging Reagents In this example, we describe how to prepare tagged (also referred to herein as "labeled") N-glycans, from glycoprotein to analysis ready sample, in 30 minutes with complete deglycosylation. Our process is a streamlined protocol that can be facilitated by a kit known as the GLYCOWORKS™ RAPIFLUOR-MS™ N-glycan Kit. Sensitivity for labeled N-glycans can be at least 2 and 100 fold increases to previous fluorescence and MS detection and can provide accurate profiling based on robust solid phase extraction ("SPE") to neutralize tetrasialylated N-glycans. Lauber, M. et al., *Rapid Preparation of Released N-Glyans for HILIC Analysis Using a Labeling Reagent that Facilitates Sensitive Fluorescence and ESI-MS Detection*, Anal. Chem. 2015, 97, 5401-5409, incorporated herein by reference.

The rapid tagging reagent facilitating our N-glycan analysis was synthesized based on rational design considerations which afford rapid labeling kinetics, high fluorescence quantum yield, and significantly enhanced MS detectability. N-glycan sample preparation can be dependent on reductive amination of aldehyde terminated saccharides. In this process, glycans are reductively aminated in anhydrous conditions in order to minimize desialylation. The sample preparation transitions from aqueous to anhydrous conditions. On the other hand, by utilizing the rapid tagging reagent, reductive amination can be eliminated through an aqueous rapid tagging reaction.

If not labeled by a rapid tagging reaction, glycans can indeed be labeled at their reducing end using reductive amination. In this reaction, a tagging reagent containing a primary amine reacts in a condensation reaction with the aldehyde group of the glycan, resulting in an imine or Schiff base, which is reduced by a reducing agent to yield a secondary amine. The reaction is often performed in dimethyl sulfoxide containing acetic acid, but alternative approaches using tetrahydrofuran and methanol have been described. Examples of an amine (also referred to herein as primary amine or compound having a primary amine) include ethanol amine, propylamine, aminobenzamide, peptides with a free amino terminus (as shown in example 5 herein), N,N-dimethylehtylene diamine, amino anthracene and amino biotin. An advantage of this labeling approach is the stoichiometric attachment of one label per glycan, allowing a direct quantitation based on fluorescence or UV-absorbance intensity.

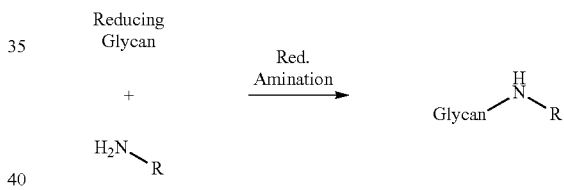

Rapid tagging of glycans can, alternatively, be readily adopted in the laboratory with the GLYCOWORKS™ RAPIFLUOR-MS™ N-glycan Kit described herein, purposefully designed to remove the bottlenecks from all aspects of N-glycan sample preparation. As shown in FIG. 1 below, the optimized N-glycan sample preparation workflow requires three steps: (1) deglycosylation to release glycans from a glycoprotein; (2) labeling to impart a detectable chemical entity to glycans; and (3) a clean-up step to remove potential interferences from the sample. These glycans are then rapidly reacted with one or more of the rapid tagging reagents and are thereby labeled with a tag comprised of an efficient fluorophore and a highly basic tertiary amine that yields enhanced sensitivity for both fluorescence and MS detection. A depiction of the structure of a rapid labeled glycan is shown immediately below. It is worth noting the rapid labeled glycans have a particularly unique linkage moiety, one that is distinct from the secondary amine linkage that comes from reductive amination reactions. Rapid labeled N-glycans will contain neutral (not acidic) urea linkages. This can impact the physicochemical characteristics and/or properties of the rapid labeled glycans, including their chromatographic retention and their fluorescence properties and other physiochemical properties such as isoelectric point ("pI"), acidity, basicity, hydrophobicity, hydrophilicity, ability to chelate metals, UV absorbance, fluorescence, absorbance in the visible spectrum, colorimetric changes, molecular size, affinity to interacting with binding partners (i.e. biotinylated residues to avidin or streptavidin, epitopes to paratopes), reduction/oxidation potential, propensity for crosslinking, cleavability (chemical and thermal), and polymeric substituents of varying length (i.e. poly ethylene glycol (PEG) 4 repeats, PEG 40 repeats).

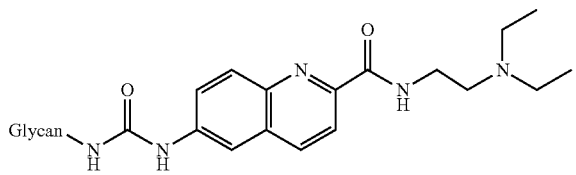

As used herein, the marks GLYCOWORKS™ and RAPIFLUOR-MS™ are owned by applicant, Waters Technologies Corporation. The mark GLYCOWORKS™ is used in connection with sample preparation kits for laboratory use comprising biological standards, sample preparation device, and disposable cartridges and chemical reagents for preparing samples for chromatography and mass spectrometry. Similarly, the mark RAPIFLUOR-MS™ is used in connection with chemical reagents for preparing samples for chromatography and mass spectrometry and in connection with sample preparation kits for laboratory use comprising biological standards, sample preparation devices, and disposable cartridges.

As such the GLYCOWORKS™ RAPIFLUOR-MS™ N-glycan Kit can be used for the fast enzymatic release and rapid labeling of N-glycans. This protocol has been validated using monoclonal antibodies and has also been tested to perform for a wide range of other N-linked glycoproteins. This sample preparation kit uses optimized deglycosylation conditions and reagents for fast release. The kit can include a rapid label reagent described U.S. Published Patent Application No. 2014/0350263, filed Aug. 13, 2014, ¶¶[0008]-[0022], [0047]-[0050], [0053]-[0182], [0191], [0228] and [0230]-[0316], incorporated herein by reference, and is designed to provide both the benefits of sensitive fluorescence detection as well as having appropriate signal intensity for mass detection.

As described herein, characterization and monitoring of N-glycosylation of proteins is significant in the detection of disease states and the manufacturing of biopharmaceuticals. Glycosylation profiles are most often assessed by means of released glycan analyses, wherein samples are often prepared by techniques that are notoriously time-consuming or lead to compromises in MS sensitivity. With the development of the GlycoWorks RapiFluor-MS N-Glycan Kit described herein, these shortcomings have been addressed by enabling unprecedented sensitivity for glycan detection while also improving the throughput of N-glycan sample preparation.

Equally important as the efficiency and sensitivity gains afforded by this new sample preparation approach, and the associated methodologies, is its robustness and its ability to produce results consistent with historical N-glycan profiling. Furthermore, glycan data generated can be used to interrogate glycan databases but first require conversion into a standardized valve called a Glucose Unit ("GU") value. Hence, another benefit of implementing a calibration standard is the ability to convert existing glycan data into a format that makes exploration of glycan databases possible. The converted data can be used in a discovery process, where samples of unknown glycan composition are under investigation. Once glycans are converted to GU values, users are able to interrogate online databases to gain insight into the potential glycan structures that may exist in their samples, potentially reducing the time required to perform a typical characterization. In liquid chromatography, calibration is performed frequently, sometimes as often as after every separation of the glycan mixture.

To detect fluorescent ("FLR") labeled glycans, hydrophilic interaction liquid chromatography ("HILIC") coupled with fluorescent detection can be used. For separation processing and in comparison to certain conventional high performance liquid chromatography ("HPLC") methods, an ethylene bridged glycan column (herein after referred as "BEH glycan column" or "BEH column") operating in HILIC mode can provide improvements in peak resolution with the ability to separate both neutral and acidic glycans. The BEH glycan column enables and produces reproducible glycan separation data and in less time spent for method optimization.

BEH columns utilize hybrid-silica BEH, bridged technology particles functionalized with a stable, amide-containing species. BEH technology has given rise to numerous particle size stationary phases ranging from 1.7 to 5 μm diameters to provide a bridge between HPLC and ultra-performance liquid chromatography ("UPLC") technology platforms. BEH particles offer peak shape and efficiency for basic analytes, a rational array of chromatographic selectivity and improvements in chemical stability at mobile phase extremes, particularly at elevated pH. The resolving power of these columns is due in part to porous particles with an optimal concentration of amide ligands for associated applications. The column can be optimized for use with either a UPLC or HPLC system having fluorescence ("FLR") detection for separating the released and labeled N-linked glycans from various bio-therapeutics, and achieve HILIC-based separations of both neutral and charged labeled glycan species.

In order to take full advantage of the BEH glycan column, or simply any HILIC-based profiling of glycans, a dextran calibration ladder (hereinafter sometimes referred to as a "dextran ladder" or "dextran ladder standard") can be used. The glycan profile obtained from a HILIC/FLR system can be calibrated against the dextran ladder and assigned with glucose unit (GU) values. For example, one such known ladder, the 2AB-labeled dextran calibration ladder, is different than other commercial offerings. The average molecular weight of the glucose homopolymer is higher (~4,500 Dalton), therefore, the "workable" GU value range is twice as much as other dextran ladder standards; the observed GU goes from 2 to 30. Hence, large glycan retention time assignment is improved. The purity and structural integrity of the dextran ladder can be assessed by both HILIC and mass spectrometry ("MS").

The elution times of glycans can be expressed in glucose units ("GU") by reference to the dextran ladder. Each individual glycan structure has a GU value which is directly related to its linkages and constituent monosaccharides. The GU value can be used to predict structures because each monosaccharide in a specific linkage contributes specifically to the GU value of a given glycan. Therefore, the dextran ladders provided herein can be used to calibrate the LC runs against day-to-day or system-to-system changes. The GU value is calculated by fitting a fifth order polynomial distribution curve or cubic spline curve to the dextran ladder, then using this curve to allocate GU values from retention times. The GU values for N-glycans can be very reproducible, with standard deviations being less than 0.3 between columns. This allows direct comparison with database values collected from a range of instruments over a period of time.

Having GU values, databases with glycans stored in values of GU can be interrogated to aid in elucidating the potential glycan structures existing within a glycan population. A dextran ladder also provides a quality controlled standard that can be used to calibrate chromatograms obtained on different instruments in different labs. Glycan retention times captured using HILIC-FLR instrumentation will vary from instrument to instrument and lab to lab. By converting retention times to GU values, the resulting data can be used to compare information between different locations both on-site and off-site. While the use of GU values is used as an example here, other chromatographic methods can benefit from the use of a dextran calibration prepared by the methods of this invention, including but not limited to reversed phase chromatography and mixed mode iterations of both reversed phase and HILIC.

Rapid labeling of N-glycans simplifies preparation of glycan samples for analysis. Yet, it is not a trivial task to produce a dextran ladder that is appropriate for use with glycans that are rapidly labeled with the rapid tagging reagent. Provided herein is a two-step process for tagging of reducing glycans that allows for tuning of chromatographic response and chemical properties, such as fluorescence and MS activity and multiple tags with differing detection properties. Each step differs in the nature of attachment to the reducing glycan. The term "reducing glycan" means reducing sugar, reducing saccharide, reducing polysaccharide (hetero-saccharide different sugar units, or different monosaccharides, or homo-saccharide) and includes any aldehyde terminated saccharide such as chitotriose, chitobiose, galactrose-β-(1-3)-GalNAc-Glycan, mannotrose-di-(N-acetyl-D-glucosamine) and maltrose. A reducing glycan or a reducing sugar is any sugar capable of acting as a reducing agent because it has a free aldehyde group. Hence the methodologies provided herein are useful in tagging or dual tagging of any compound containing an aldehyde (also referred to sometimes as an aldehyde group) including O-glycans.

As shown immediately below, the first step utilizes a reductive amination process comprising the step of reacting a reducing glycan (an aldehyde terminated saccharide) with a compound having a primary amine to produce an intermediate compound such as ethanol amino dextran ladder, propylamino dextran ladder or other compound having an aldehyde that has been converted to a secondary amine, or a reducing glycan (reducing saccharide) converted to be terminated with a secondary amine. Primary amines (also referred to herein as "compound having a primary amine" or amine) which can display a desired characteristic in order to produce the intermediate compound or a compound where its aldehyde is converted to a secondary amine include ethanol amine, propylamine, aminobenzamide, peptides with a free amino terminus (as shown in example 5 herein), N,N-dimethylehtylene diamine, amino anthracene and amino biotin. The second step is a reaction with the rapid tagging reagent that can impart differing properties. In other words, characteristics of the intermediate compound are different from the rapid tagged compound (i.e., rapid tagged glycan).

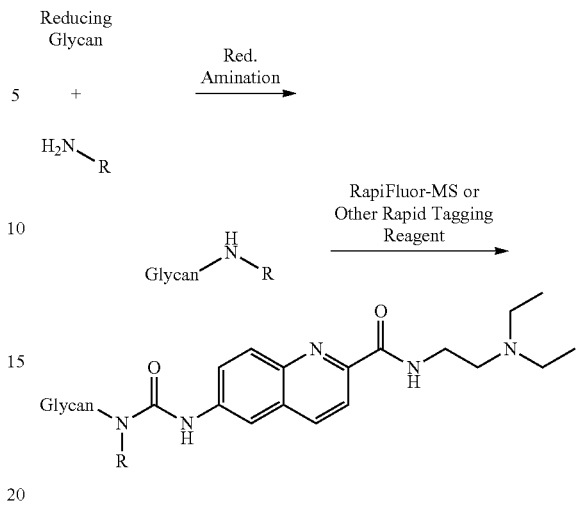

Where R—NH$_2$ is ethanol amine or similar type of compound having a primary amine.

Figure 2:
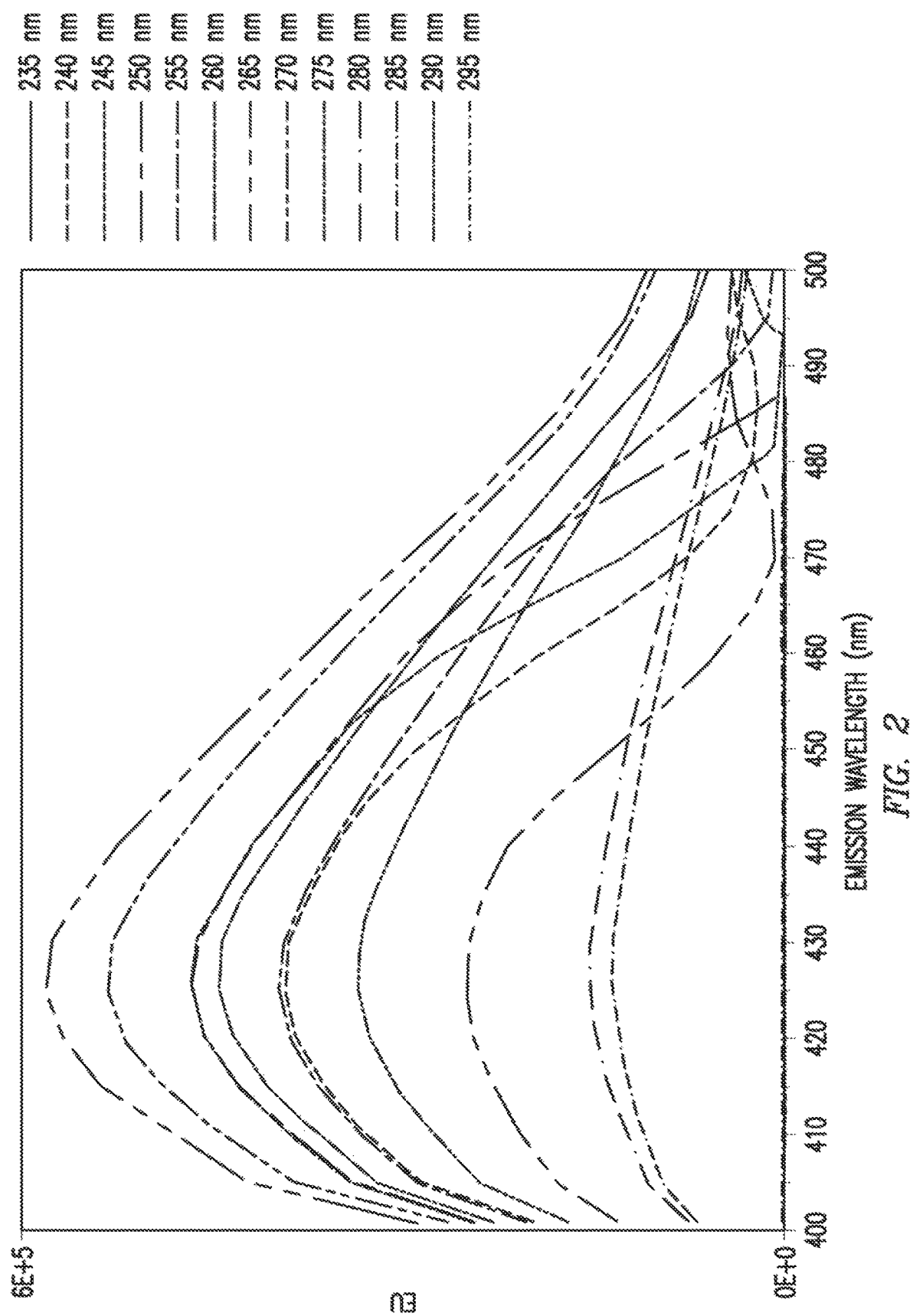
FIG. 2 shows fluorescence emission spectra for a rapid labeled N-glycan labeled with a rapid tagging reagent having optimized wavelengths of 265 nm for excitation and 425 nm for emission.

This methodology initially arose out of a need to match optical properties between N-linked glycans tagged with the rapid tagging reagent (FIG. 2) to the properties of a dextran standard (also referred to herein as a reducing sugar) (FIG. 3) tagged via only reductive amination using a precursor as shown immediately below:

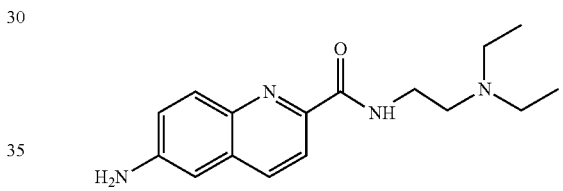

Between these two material types, it was found that fluorescence properties, namely excitation and emission maxima, are disadvantageously different. As a consequence, such a dextran ladder was not a suitable calibrant for the analysis of rapid labeled glycans in liquid chromatography.

The methodologies provided herein utilize a reaction route to tagging of reducing glycans (or any glycan that is aldehyde terminated) with a rapid tagging/amine reactive label to provide detection of the N glycan through its fluorescent and/or MS active properties. Traditional tagging of reducing glycans involves reductive amination (a lengthy process, i.e., 1 to 4 hours and possibly as long as 8 hours for high yield) with a specific tagging reagent. While, the present methodologies utilize reductive amination, once the intermediary amine is produced, a second step (fast, ~5 min) is taken to introduce the tag (or label) having the fluorescent/MS active properties and provide saccharide molecules of the following structure Formula I. As provided in this embodiment, the terminal monosaccharide residue is shown to be an N-acetylated glucosamine (GlcNAc) that is linked to the remaining saccharide structure through its 4-OH position. The terminal monosaccharide residue does not have to be a GlcNAc, however; the dextran ladder can be terminated with a glucose monosaccharide that links to the structure through its 6-OH position. In addition, the terminal monosaccharide residue can be linked through the 4-OH position. The dextran ladder can be terminated with any glucose monosaccharide that links to the remaining saccharide structure through its 6-OH position as exemplified in Formula II below.

Formula I

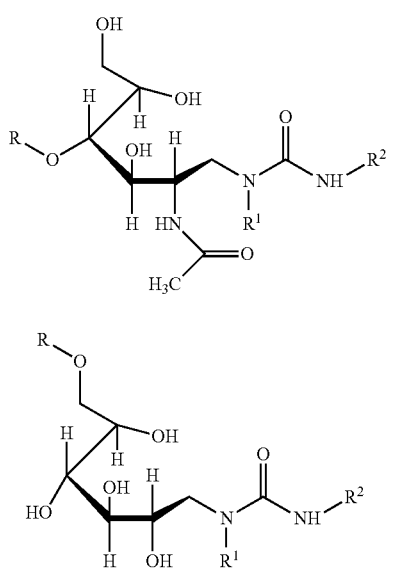

Formula II where R can be monosaccharide units or glucose residues, $R_1$ is —CH$_2$CH$_2$OH and $R_2$ is the portion of the rapid tagging reagent which incorporates the FLR-MS functionality into the structure, and is exemplified with the following structures:

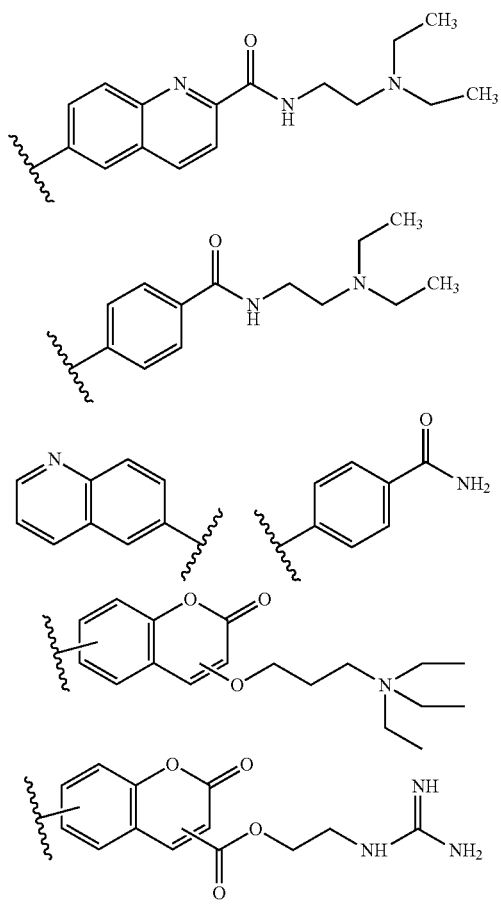

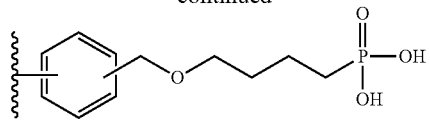

The methodologies provided herein allow for tagging of reducing glycans with the rapid tagging agent which has the same optical and MS properties as other molecules that have been labeled with the rapid tagging reagent. In other words, carrying out reductive amination with the primary amine of the rapid tagging reagent can produce a molecule that differs in absorbance and emission properties from comparable molecules labeled with the rapid tagging agent (N-linked molecules). The linkers can be different (amine vs urea), resulting in changes in chromophore properties. By carrying out reductive amination with a compound having a primary amine, then tagging the amine with the rapid tagging reagent, the optical properties are maintained.

Figure 4A:
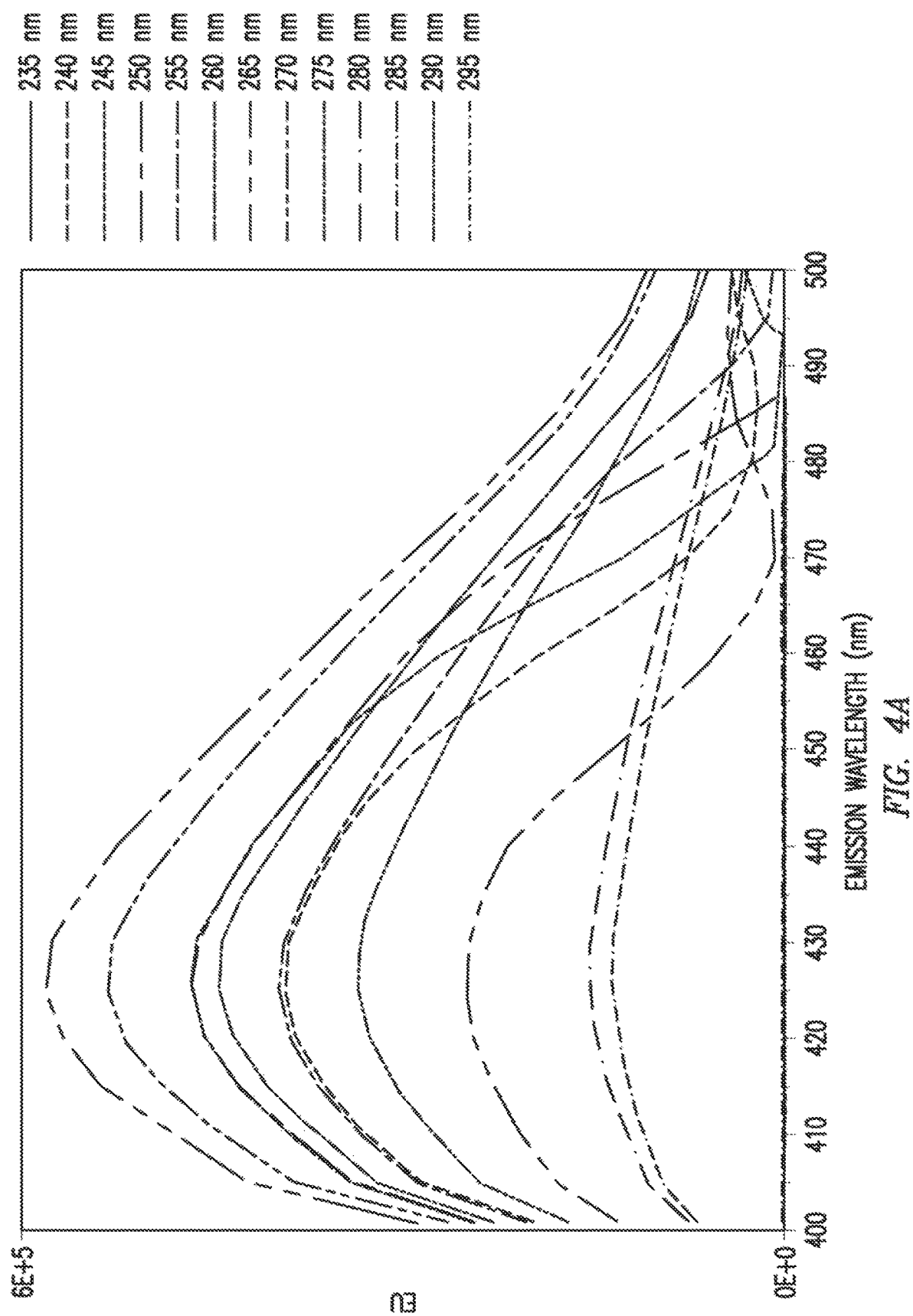
FIGS. 4A and 4B show fluorescent properties of a rapid labeled dextran ladder produced with the methods provided herein.

FIG. 4A show optical properties of the rapid labeled dextran ladder produced by the methods described herein where the rapid tagging reagent is:

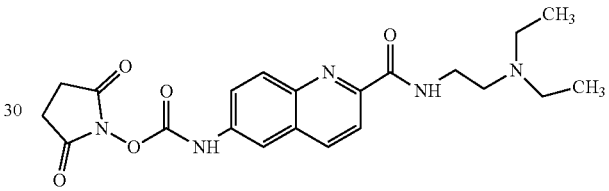

Figure 4B:
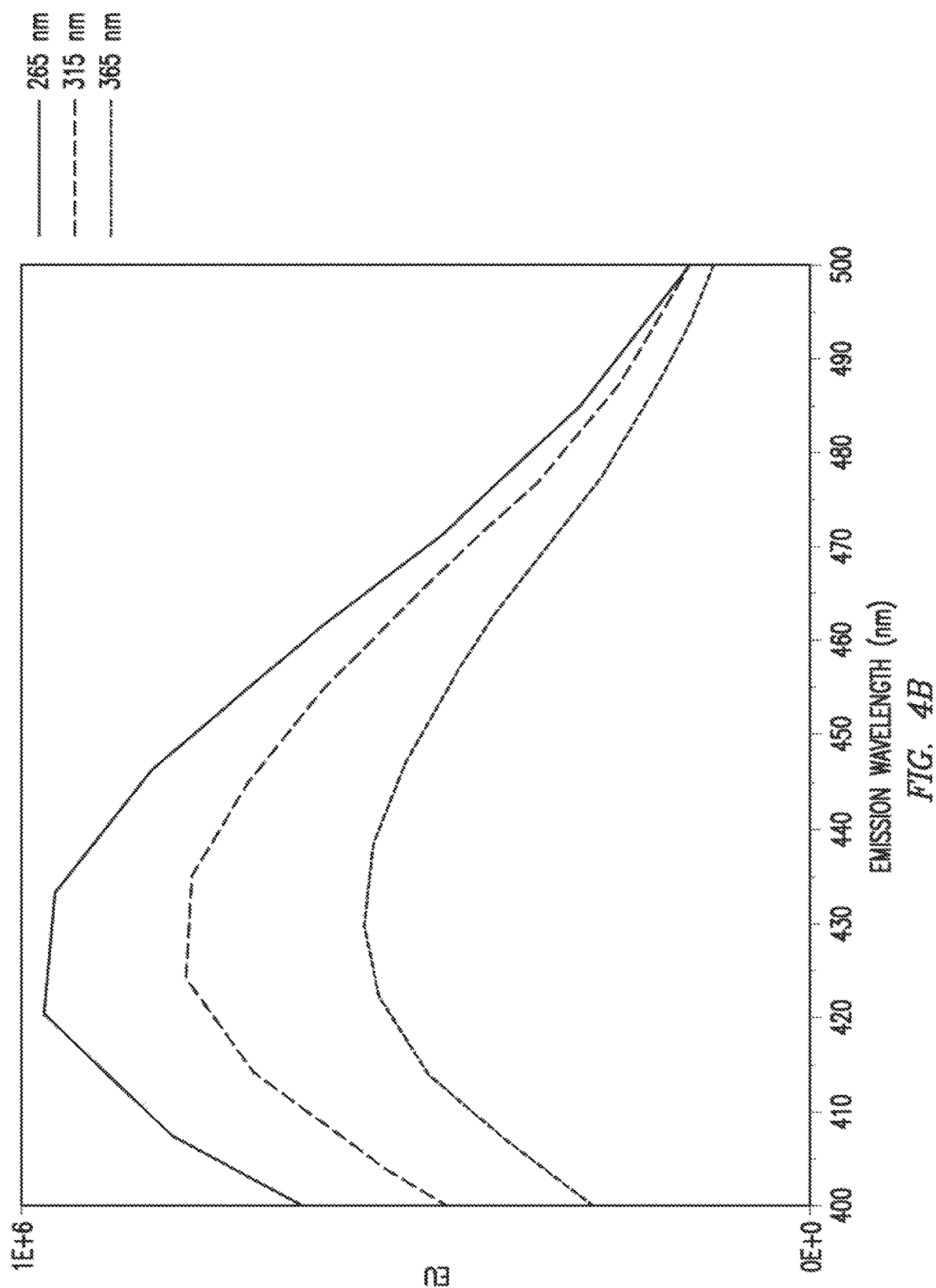

RapiFluor-MS or RFMS
2,5-dioxopyrrolidin-1-yl (2-((2-(diethylamino)ethyl)carbamoyl) quinolin-6-yl)carbamate FIG. 4B shows that the dextran ladder has substantially identical fluorescence properties as that of the rapid labeled glycan produced with the same rapid tagging reagent, the rapid labeled glycan which is exemplified below:

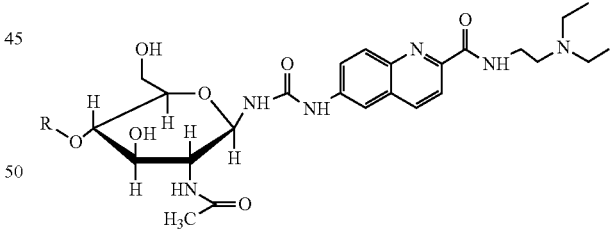

A Rapid Labeled Glycan

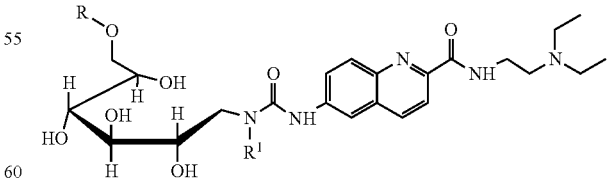

A Rapid Labeled Dextran Ladder

The present methodologies allow for adjusting the relative retention of a glucose homopolymer (referred herein as a "dextran ladder") through changes in overall polarity. For example, tagging of the dextran ladder through reductive amination with a) ethanolamine or b) propylamine, followed by reaction with the rapid tagging reagent, results in differing retention characteristics. Thus, the chromatographic retention characteristics, among other characteristics, of the dextran ladder can be tuned as a calibration standard.

Accordingly, the present methodologies can produce a dextran ladder having chemical properties highly similar to those of N-glycans that are labeled with a rapid tagging labeling reagent.

As provided in the proposed procedures set out in Example 3, one embodiment of such a glucose homopolymer includes reductive amination with ethanolamine followed by labeling with the rapid tagging reagent to produce a rapid labeled ethanolamino dextran ladder (an embodiment of a rapid labeled dextran ladder) shown immediately below:

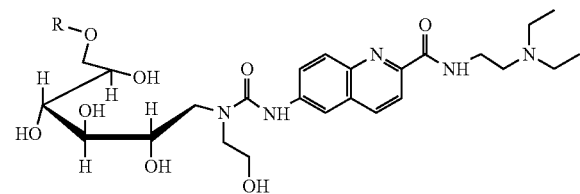

Figure 7A:
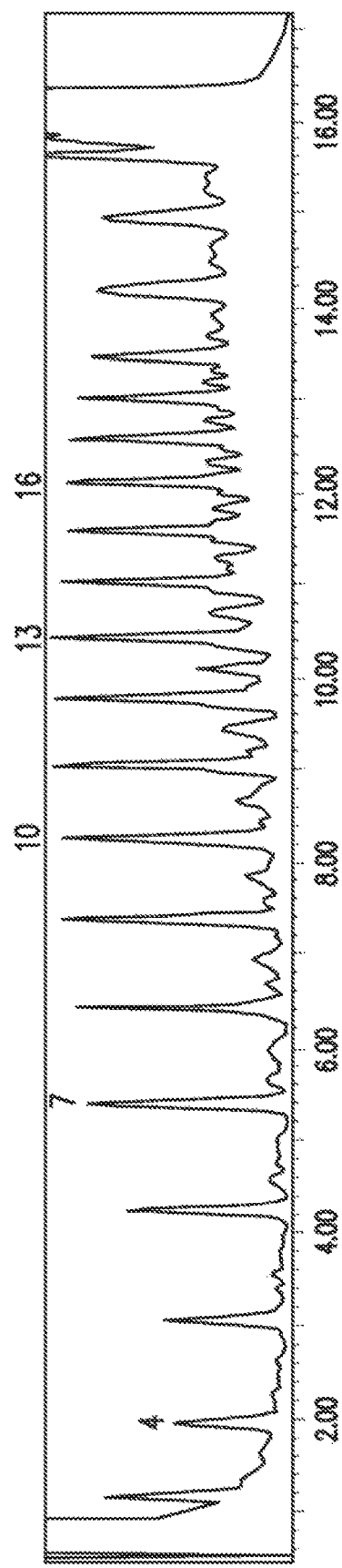
FIGS. 7A and 7B show the fluorescence chromatogram obtained for a rapid labeled, propylamino dextran versus a rapid labeled ethanolamino dextran using a glycan BEH amide 2.1×50 mm column.

In another embodiment, the ethanolamine in the procedures set out in Example 3 can be replaced with propylamine. The resulting rapid labeled propylamino dextran (shown below) exhibits altered chromatographic retention when separated with a BEH Amide stationary phase as shown in FIG. 7A versus that shown in FIG. 7B.

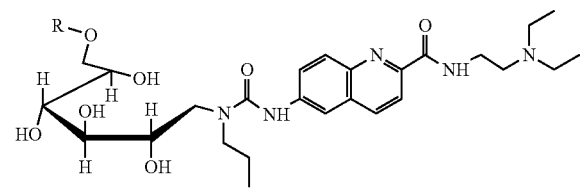

Rapid Labeled Propylamino Dextran, a Rapid Labeled Dextran Ladder

Example 2

Preparation of the Rapid Labeled Dextran Ladder Reductive Amination of Dextran, Coupling Procedure 100 mg of Dextran 5000 is accurately weighed and placed in an 8 mL. 2800 µl of DMSO is then piped into the 8 mL vial and stirred until the dextran is dissolved. The actual weight is then recorded.

Add 1200 µl of glacial acid to the 8 ml vial followed by 90.0 mg (91.0 ml) of redistilled ethanolamine (MW=61.08, d=1.012) and then add 128 mg of sodium cyanoborohydride. Gently mix the slurry and incubate for 3 hours at 70° C. in a heat block with magnetic stirring. Following the 3 hour incubation, the resulting reaction is removed from the heat block and cooled to a temperature below 40° C. Transfer the reaction contents from the 8 ml vial into a tared 50 ml centrifuge and add 40 ml of ACN. Measure and Record the Tare Weight, and place the vial in a refrigerator for 30 minutes. Then, centrifuged the mixture at 4000 RPM for 5 minutes and decant the supernatant. Re-suspend the pellet in 40 ml ACN and vortex vigorously. Repeat the steps of centrifugation, decantation and re-suspension for a total of three washes. The 30 minute stand is not required. Dry the pellet under a stream of nitrogen for 20 minutes and then overnight under vacuum at room temperature. Weigh the pellet to determine final recovery. Record the Final weight, Tare Weight and Recovered Weight.

Procedure for Rapid Labeling to Produce the Ethanolamino Labeled Dextran Ladder

This procedure is designed for the rapid tagging reaction to be performed at a 100-200 fold molar excess of the rapid tagging reagent. Dissolve 4.0±0.3 mg of the ethanolamino dextran in 500 µl of 50 mM HEPES, pH 7.9 (titrated from free acid with sodium hydroxide). Add 300 µl of anhydrous DMF. Use this dextran solution to dissolve 100±0.5 mg of rapid tagging reagent. Allow the reaction to proceed at room temperature for 10 minutes. Periodically (every 20 to 30 seconds), stir/agitate the reaction mixture. At the completion of the incubation at room temperature, dilute the reaction with 7.6 ml ACN. A best practice is to dilute the reaction right before loading onto the SPE cartridge.

HILIC SPE Clean-Up

Wash with 6 ml of water and 6 ml equilibration with 85% ACN. Load the ACN diluted reaction mixture in two (2) 4.5 ml volumes (approximate volume) onto a cartridge. Washed three times 6 ml volumes of 1:9:90 formic acid/water/ACN. Elute with three (3) 4 ml volumes of 200 mM ammonium acetate without pH adjustment, 5% ACN. Dispense 600 µl volumes and dry via centrifugal vacuum evaporation.

The above procedure can result in yields of the labeled dextran ladder prepared from ethanolamino dextran intermediate up to about 80 standards per batch.

Example 3

Experimental Conditions and Representative Data for Rapid Labeled Ethanolamino Dextran, a Rapid Labeled Dextran Experimental Conditions for Batches 1 to 3 of rapid labeled Ethanolamino Dextran, a Rapid Labeled Dextran-Liquid chromatography was used to analyze the fluorescence and MS properties of the labeled dextran ladder as prepared in Example 2. The column was flushed in 70% HPLC grade acetonitrile (ACN)/30% HPLC grade water v/v. The column was then equilibrated with mobile phase conditions before making first injection. Table 2 and Table 3 immediately below provide HILIC UPLC/FLR/MS conditions used in the analysis.

TABLE 2

| System | ACQUITY UPLC ® H-Class Bio System with an ACQUITY UPLC ® FLR Detector/ Synapt G2-S |
|---|---|
| Column | ACQUITY UPLC ® Glycan BEH Amide, 130 Å, 1.7 µm, 2.1 × 150 mm |
| Temperature | 60° C. |
| Mobile Phase A | 50 mM Ammonium Formate, pH 4.5 |
| Mobile Phase B | 100% acetonitrile (ACN) |
| Flow Rate | 0.4 mL/min |

| | Time (min) | Flow Rate (mL/min) | % A | % B | Curve |
|---|---|---|---|---|---|
| Gradient | 0.0 | 0.4 | 25 | 75 | 6 |
| | 40.0 | 0.4 | 49 | 51 | 6 |
| | 41.5 | 0.2 | 100 | 0 | 6 |

TABLE 2-continued

| | | | | |
|---|---|---|---|---|
| 44.5 | 0.2 | 100 | 0 | 6 |
| 48.1 | 0.2 | 25 | 75 | 6 |
| 52.6 | 0.4 | 25 | 75 | 6 |
| 60.0 | 0.4 | 25 | 75 | 6 |

| | |
|---|---|
| FLR wavelength | EX 265/EM 425 nm |
| FLR sampling rate | 2 Hz |
| Injection volume | 1 µL |

TABLE 3

Mass Spectrometry

| | |
|---|---|
| Capillary | 3.0 Kv |
| Cone | 80 V |
| Source offset | 50 V |
| Extraction cone | 4 V |
| Desolvation gas | 800 L/hr |
| Nebulizer | 6 bar |
| Source Temperature | 120° C. |
| Desolvation Temperature | 350° C. |
| Sampling Rate | 1 Hz |
| Flow Rate | 5 µL/min |
| Acquisition Rate | 100-2500 m/z |
| LockMass Calibration | 0.1 µM Glu-fibrinopeptide B in 50:50 water/ACN, 0.1% (v/v) FA (real-time mass correction) |

Figure 5A:
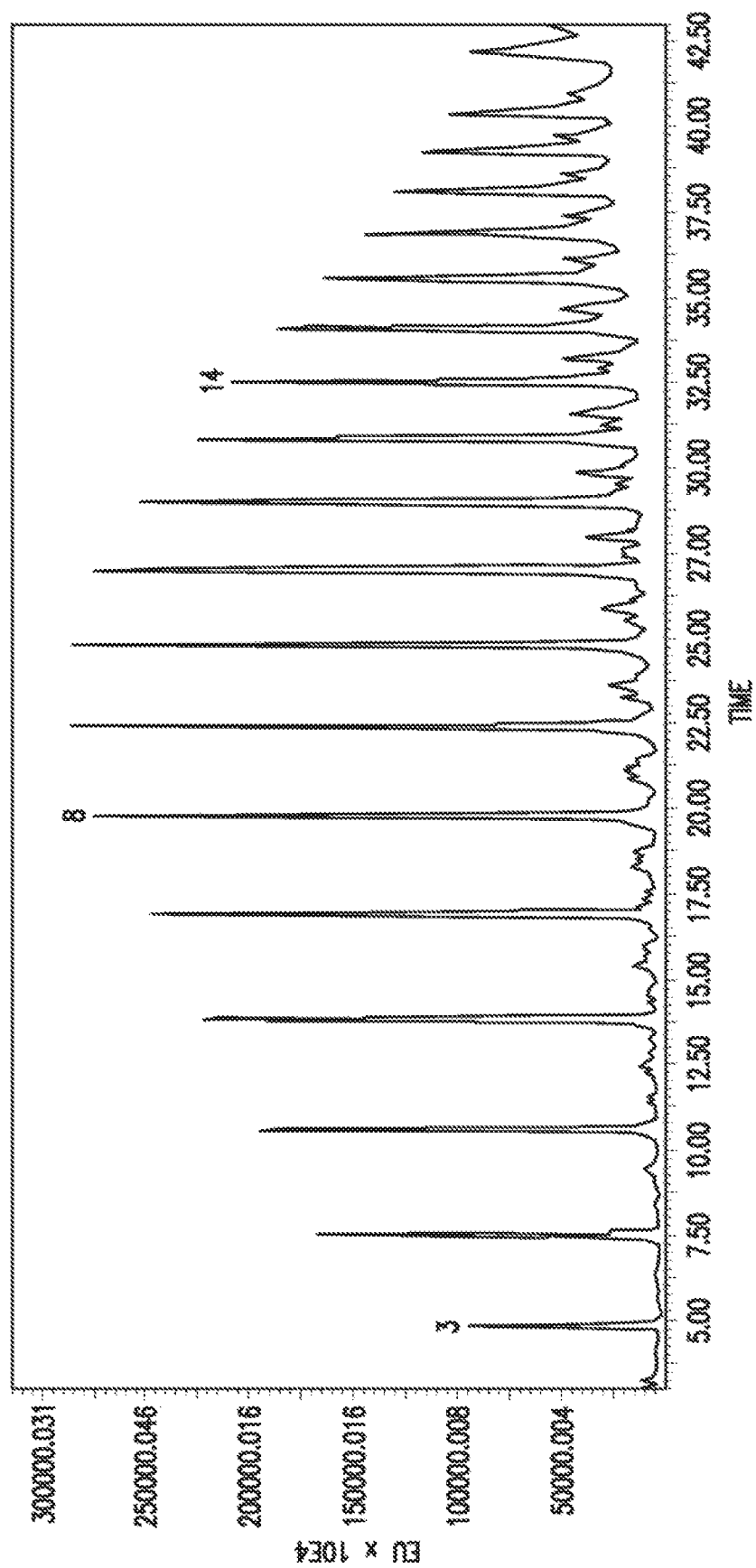
FIGS. 5A, 5B and 5C show representative HILIC fluorescence chromatograms for a rapid labeled ethanolamino dextran ladder produced via the methods provided herein.
Figure 5B:
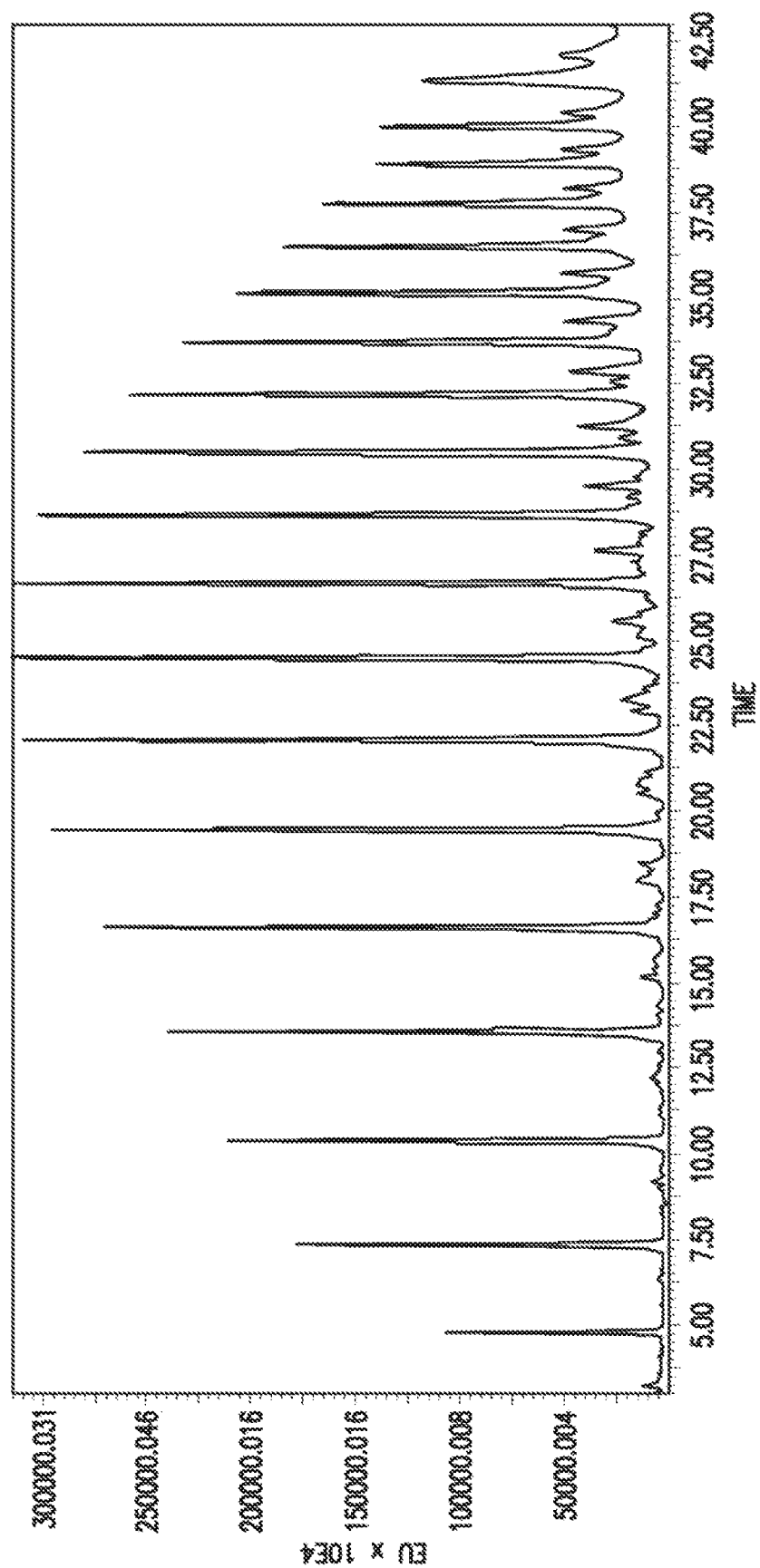
Figure 5C:
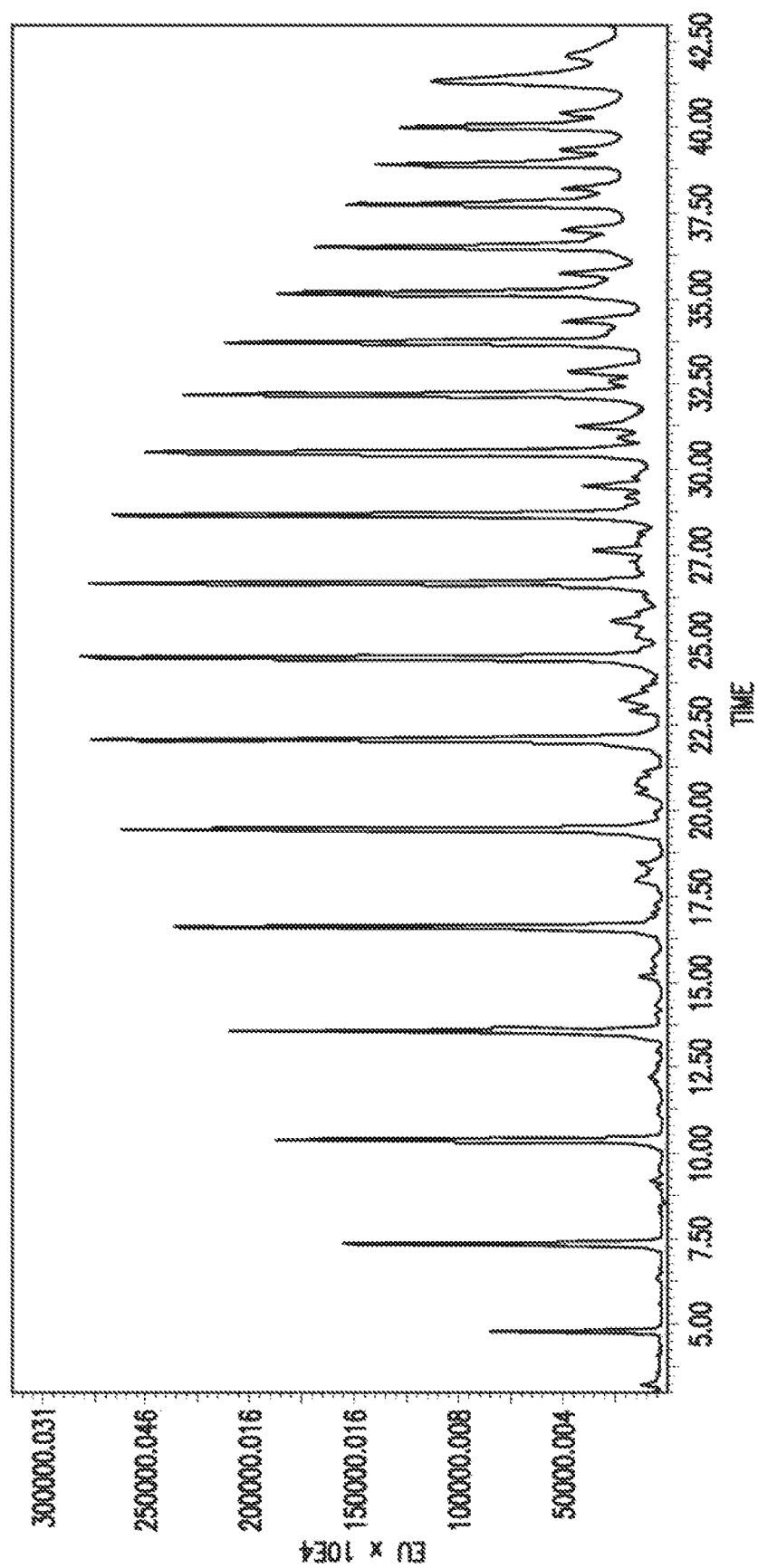
Figure 6A:
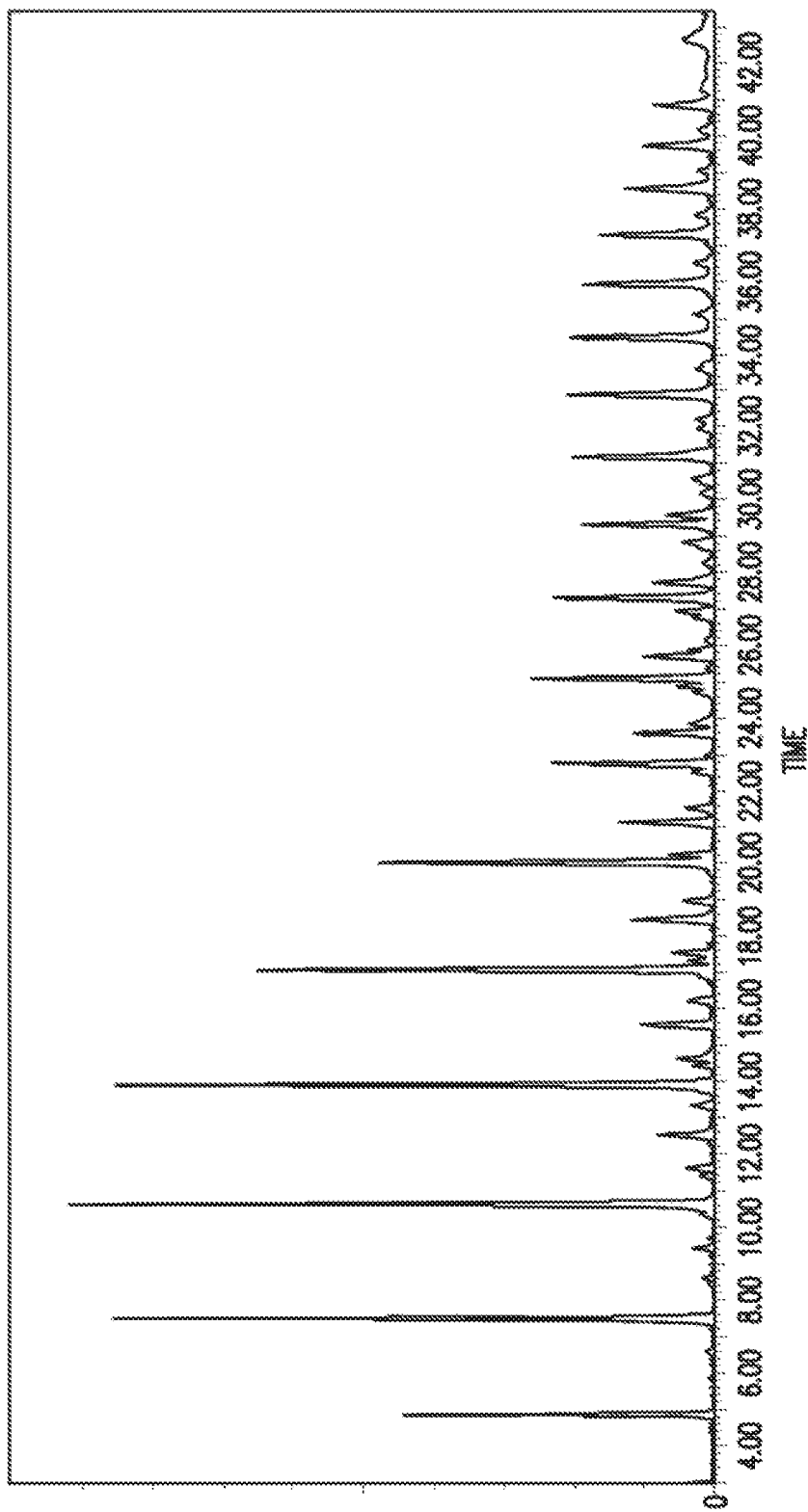
FIGS. 6A, 6B and 6C show the corresponding Base Peak Ion ("BPI") chromatograms for each batch of the rapid labeled dextran ladders of Example 3.
Figure 6B:
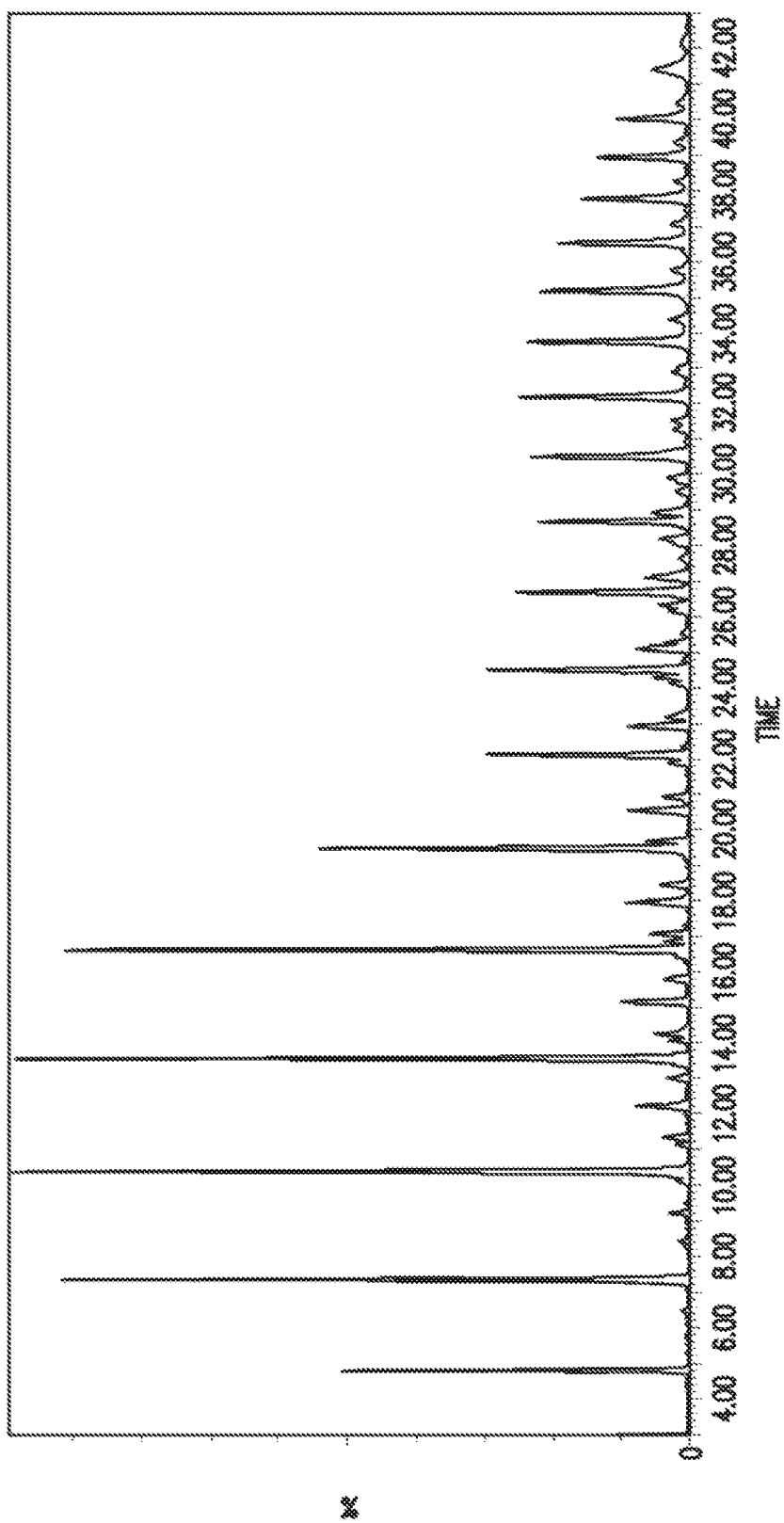
Figure 6C:
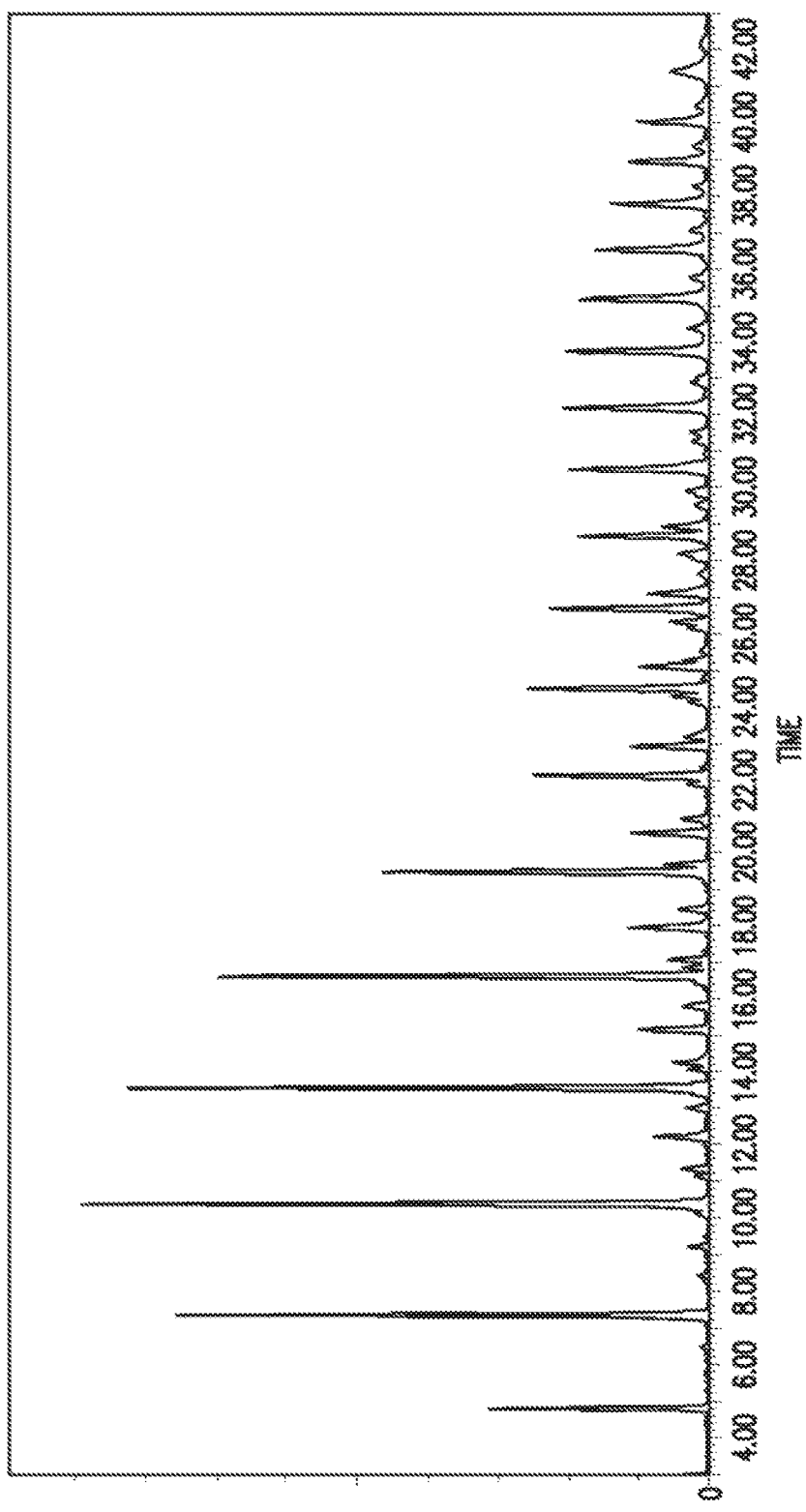

FIGS. 5A, 5B and 5C show the fluorescence chromatograms for each of the three batches of the labeled (ethanolamino) dextran ladder prepared. FIGS. 6A, 6B and 6C show the corresponding Base Peak Ion (BPI) chromatograms for each batch of rapid labeled dextran ladder. The masses of labeled Glucose Units (GU) species are shown in Table 4.

TABLE 4

| GU | Labeled Dextran Ladder | m/z (monoisotropic) [M + H]+ | m/z (monoisotropic) [M + 2H]2+ |
|---|---|---|---|
| 2 | 699.333 | 700.340 | 350.674 |
| 3 | 861.391 | 862.398 | 431.703 |
| 4 | 1023.449 | 1024.456 | 512.732 |
| 5 | 1185.507 | 1186.514 | 593.761 |
| 6 | 1347.565 | 1348.572 | 674.790 |
| 7 | 1509.623 | 1510.630 | 755.819 |
| 8 | 1671.681 | 1672.688 | 836.848 |
| 9 | 1833.739 | 1834.746 | 917.877 |
| 10 | 1995.797 | 1996.804 | 998.906 |
| 11 | 2157.855 | 2158.862 | 1079.935 |
| 12 | 2319.913 | 2320.920 | 1160.964 |
| 13 | 2481.971 | 2482.978 | 1241.993 |
| 14 | 2644.029 | 2645.036 | 1323.022 |
| 15 | 2806.087 | 2807.094 | 1404.051 |
| 16 | 2968.145 | 2969.152 | 1485.080 |
| 17 | 3130.203 | 3131.210 | 1566.109 |
| 18 | 3292.261 | 3293.268 | 1647.138 |
| 19 | 3454.319 | 3455.326 | 1728.167 |
| 20 | 3616.377 | 3617.384 | 1809.196 |

Example 4

Modulating Chromatographic Retention with the Compound Having Primary Amine Via Reductive Amination A second rapid labeled dextran was prepared by replacing ethanolamine set out in EXAMPLE 2 with propylamine. The chromatographic retention of the resulting rapid labeled, propylamino dextran was compared with that of the previously mentioned rapid labeled, ethanolamino dextran according to the experimental conditions outlined below:

The column was flushed in 70% HPLC grade acetonitrile (ACN)/30% HPLC grade water v/v. The column was then equilibrated with mobile phase conditions before making first injection. Table 5 provides the HILIC UPLC/FLR conditions used in the analysis.

TABLE 5

| | | | | |
|---|---|---|---|---|
| System | ACQUITY UPLC ® H-Class Bio System with an ACQUITY UPLC ® FLR Detector | | | |
| Column | ACQUITY UPLC ® Glycan BEH Amide, 130 Å, 1.7 µm, 2.1 × 50 mm | | | |
| Temperature | 60° C. | | | |
| Mobile Phase A | 50 mM Ammonium Formate, pH 4.5 | | | |
| Mobile Phase B | 100% acetonitrile (ACN) | | | |
| Flow Rate | 0.4 mL/min | | | |

| | Time (min) | Flow Rate (mL/min) | % A | % B | Curve |
|---|---|---|---|---|---|
| Gradient | 0.0 | 0.4 | 25 | 75 | 6 |
| | 40.0 | 0.4 | 49 | 51 | 6 |
| | 41.5 | 0.2 | 100 | 0 | 6 |
| | 44.5 | 0.2 | 100 | 0 | 6 |
| | 48.1 | 0.2 | 25 | 75 | 6 |
| | 52.6 | 0.4 | 25 | 75 | 6 |
| | 60.0 | 0.4 | 25 | 75 | 6 |

| | |
|---|---|
| FLR wavelength | EX 265/EM 425 nm |
| FLR sampling rate | 10 Hz |
| Injection volume | 1 µL |

Figure 7B:
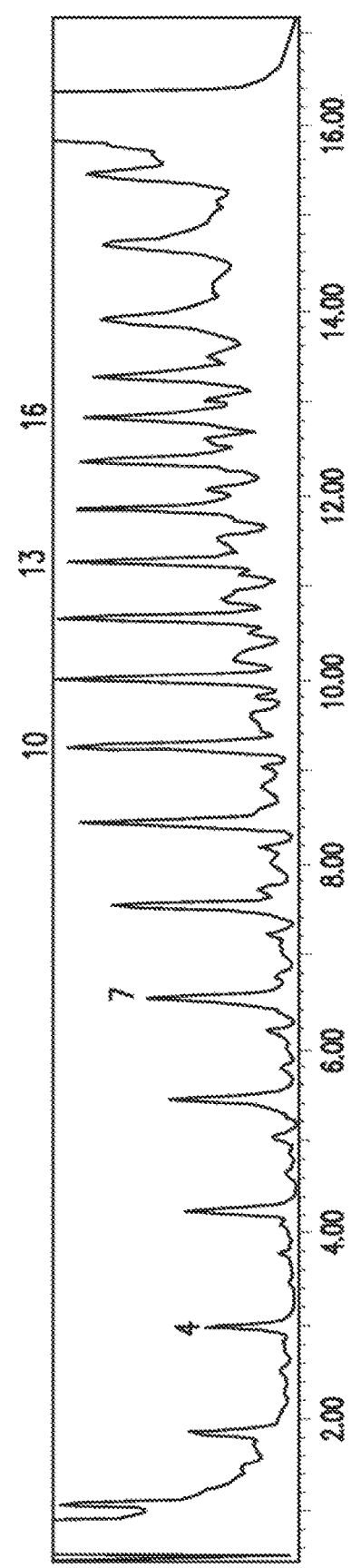

FIGS. 7A and 7B show the fluorescence chromatogram obtained for rapid labeled, propylamino dextran versus rapid labeled ethanolamino dextran when using a BEH Amide 2.1×50 mm column.

Prophetic Example 5

Incorporating Multiple Functionalities onto a Reducing Saccharide

More broadly, the presented methodology can impart certain chemical properties onto reducing glycans and sugars via incorporation of separate labeling moieties (or also referred to herein as "tags" or "labels"), one via reductive amination and another by rapid tagging processing.

In an embodiment of the present methodologies, a twice labeled N-glycan can be purified from sample matrices via streptavidin pull-down and then subsequently detected via the rapid tagging reagent to impart fluorescence and/or enhanced ionization efficiency. This "twice-labeled" saccharide shown below can have a biotin label along with a highly fluorescent, MS active label. In an embodiment shown immediately below, an amino biotin molecule could be used for reductive amination and the reductively aminated saccharide could be labeled via a rapid tagging reaction.

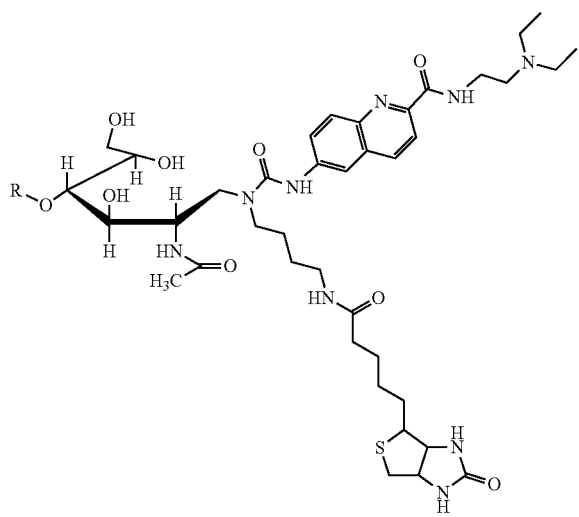

Rapid Labeled, Biotinylated Saccharide

In an embodiment, more than one fluorophore/chromophore can be used to enable multiple wavelength detection on a single saccharide species, as would be possible if this methodology was applied to reductively aminate a glycan with aminobenzamide and to thereafter label it with the rapid tagging reagent.

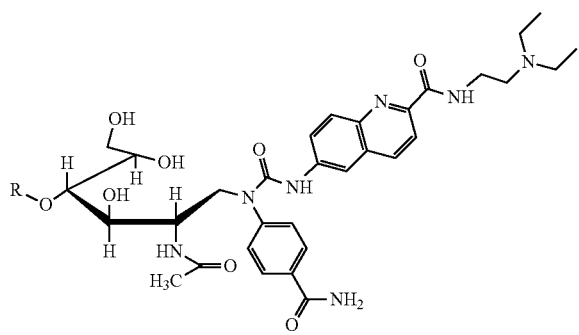

The present methodology could also allow saccharides/glycans to be labeled with an epitope tag such that immunoaffinity enrichment or immuno based detection is enabled. In one particular embodiment, a saccharide can be reductively aminated with a hemagglutinin (HA) epitope tag, a peptide of sequence YPYDVPDYA, and then labeled with the rapid tagging reagent.

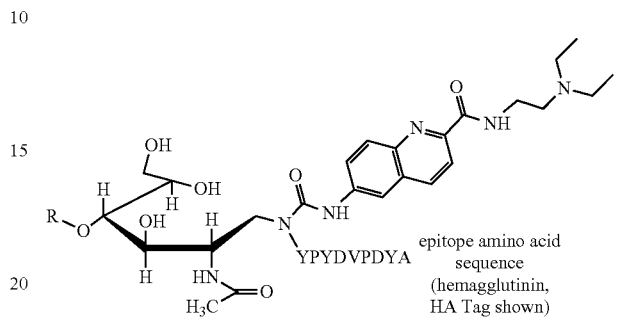

epitope amino acid sequence (hemagglutinin, HA Tag shown)

We claim:

1. A method of making a calibrant useful in liquid chromatography, comprising the steps of:

providing a reducing glycan having an aldehyde group;

reacting the aldehyde group of the reducing glycan with a compound having a primary amine through a reductive amination to produce an intermediary compound;

mixing the intermediary compound with a rapid tagging reagent, wherein the intermediary compound is rapidly labeled with the rapid tagging reagent; and physically producing a rapid labeled dextran ladder having identical optical properties as a rapid labeled N-glycan wherein the rapid label N-glycan is produced by rapid tagging of a N-glycan with the rapid tagging reagent.

* * * * *